United States Patent
Takada et al.

(10) Patent No.: US 12,102,470 B2
(45) Date of Patent: Oct. 1, 2024

(54) RADIATION SOURCE POSITION ESTIMATION SYSTEM, CALIBRATION SYSTEM AND BIOMAGNETIC MEASURING SYSTEM

(71) Applicants: Masahiro Takada, Tokyo (JP); Yoshihisa Naijo, Kanagawa (JP); Akira Kinoshita, Tokyo (JP)

(72) Inventors: Masahiro Takada, Tokyo (JP); Yoshihisa Naijo, Kanagawa (JP); Akira Kinoshita, Tokyo (JP)

(73) Assignee: Ricoh Company, Ltd., Tokyo (JP)

(*) Notice: Subject to any disclaimer, the term of this patent is extended or adjusted under 35 U.S.C. 154(b) by 428 days.

(21) Appl. No.: 17/609,141

(22) PCT Filed: Jun. 23, 2020

(86) PCT No.: PCT/JP2020/024655
§ 371 (c)(1),
(2) Date: Nov. 5, 2021

(87) PCT Pub. No.: WO2020/262401
PCT Pub. Date: Dec. 30, 2020

(65) Prior Publication Data
US 2022/0218300 A1     Jul. 14, 2022

(30) Foreign Application Priority Data
Jun. 27, 2019  (JP) ................................. 2019-120422
Sep. 12, 2019  (JP) ................................. 2019-166562

(51) Int. Cl.
*A61B 6/58*     (2024.01)
*A61B 5/242*    (2021.01)
(Continued)

(52) U.S. Cl.
CPC .............. *A61B 6/584* (2013.01); *A61B 5/242* (2021.01); *A61B 6/547* (2013.01); *A61B 6/588* (2013.01);
(Continued)

(58) Field of Classification Search
CPC ................................ A61B 6/584; A61B 6/547
See application file for complete search history.

(56) References Cited

U.S. PATENT DOCUMENTS 10,885,629 B2     1/2021  Takada et al.
2004/0245447 A1*  12/2004 Karasawa ............. A61B 6/583
                                                  378/207
(Continued)

FOREIGN PATENT DOCUMENTS

| JP | H05-277082 | 10/1993 |
|----|------------|---------|
| JP | 2990944    | 12/1999 |

(Continued)

OTHER PUBLICATIONS

JP 2000-37361 A with English translation (Year: 2000).*
(Continued)

*Primary Examiner* — Chih-Cheng Kao
(74) *Attorney, Agent, or Firm* — IPUSA, PLLC

(57) ABSTRACT

A disclosed radiation source position estimation system includes a first position information specifier configured to specify position information of one or more elements included in a position measuring member; an imager configured to acquire images of the one or more elements formed by radiation emitted from a radiation source; and a second position information specifier configured to specify position information of the radiation source, based on the first position information specified by the first position information specifier and the images acquired by the imager.

12 Claims, 19 Drawing Sheets

(51) Int. Cl.
*A61B 6/00* (2024.01)
*B82Y 25/00* (2011.01)
*G01R 33/035* (2006.01)

(52) U.S. Cl.
CPC .............. *A61B 6/589* (2013.01); *B82Y 25/00* (2013.01); *G01R 33/035* (2013.01)

(56) References Cited

U.S. PATENT DOCUMENTS

| | | | |
|---|---|---|---|
| 2006/0245628 A1* | 11/2006 | Jeung | G01T 7/005 382/128 |
| 2009/0213997 A1 | 8/2009 | Maschke | |
| 2010/0016712 A1 | 1/2010 | Bartal et al. | |
| 2019/0005660 A1 | 1/2019 | Kinoshita et al. | |
| 2019/0167135 A1 | 6/2019 | Okada et al. | |
| 2019/0236777 A1 | 8/2019 | Takada et al. | |
| 2019/0374188 A1 | 12/2019 | Yamagata | |

FOREIGN PATENT DOCUMENTS

| | | |
|---|---|---|
| JP | 2000-037361 | 2/2000 |
| JP | 2012-081000 | 4/2012 |
| JP | 4977436 | 7/2012 |
| JP | 2017-169627 | 9/2017 |
| JP | 2018-089104 | 6/2018 |
| JP | 2019-013724 | 1/2019 |
| JP | 2019-098156 | 6/2019 |
| JP | 2019-130275 | 8/2019 |

OTHER PUBLICATIONS

International Search Report issued on Sep. 21, 2020 in PCT/JP2020/024655.
Japanese Office Action for 2019-166562 mailed on Jun. 13, 2023.
Office Action dated Feb. 28, 2024 issued with respect to the corresponding European Patent Application No. 20739473.5.

* cited by examiner

[Fig. 4]
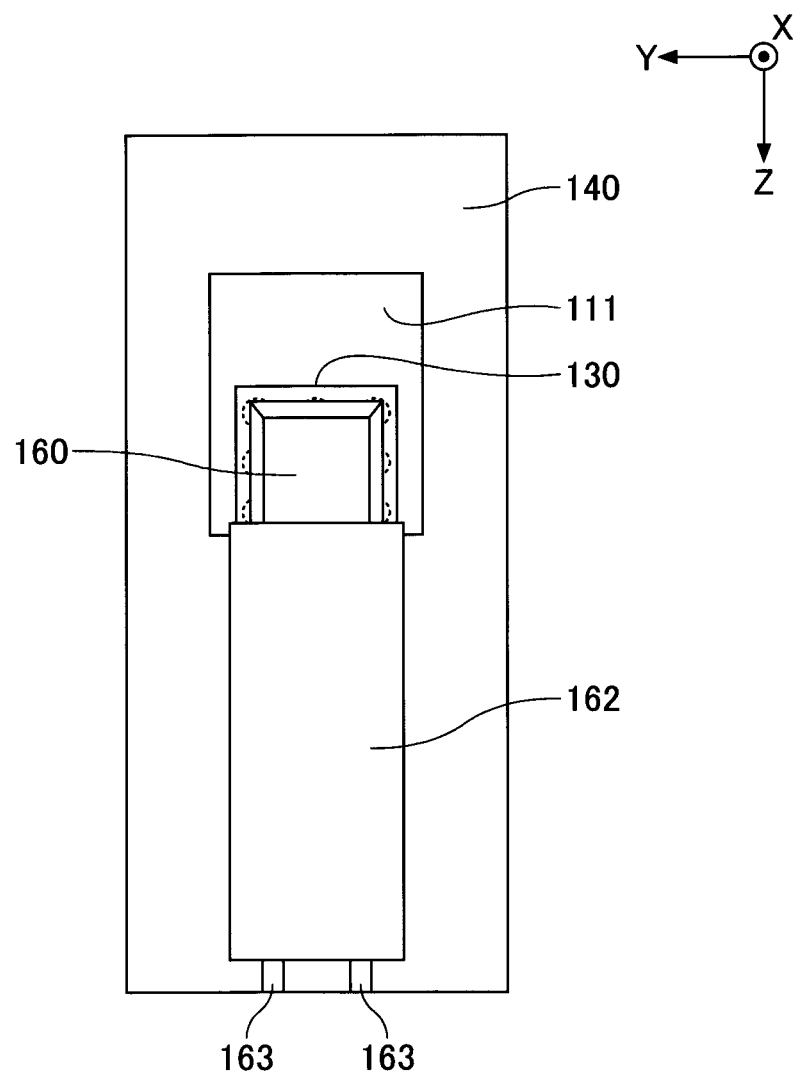

[Fig. 5]
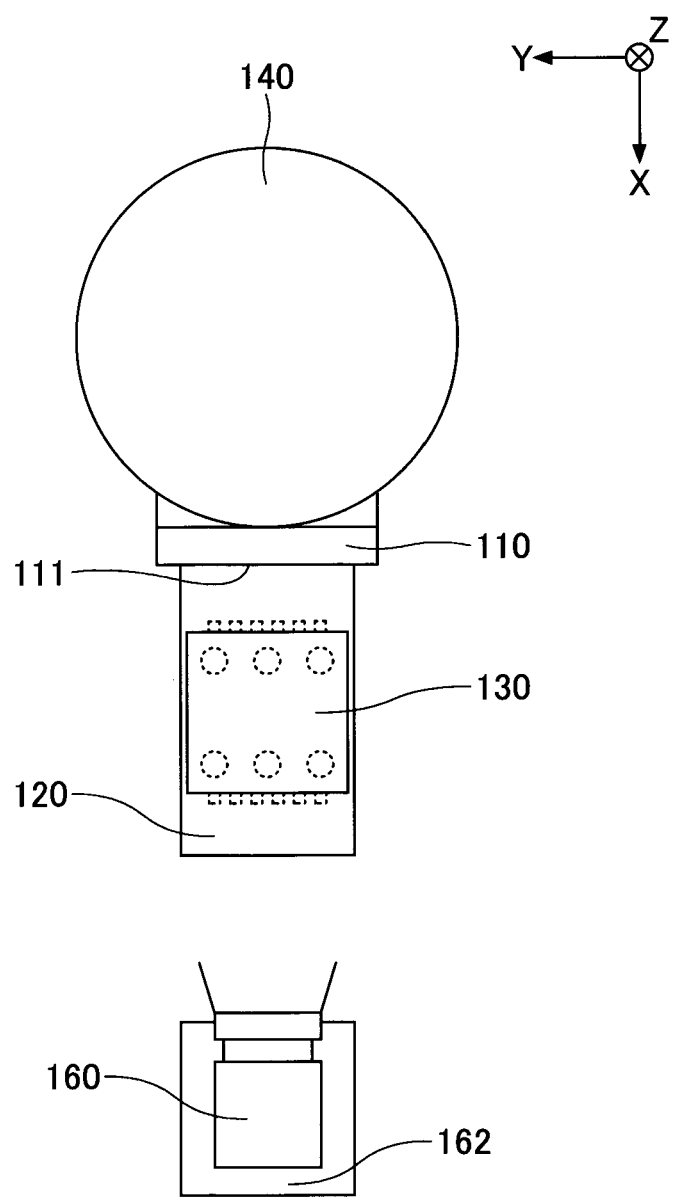

[Fig. 6]
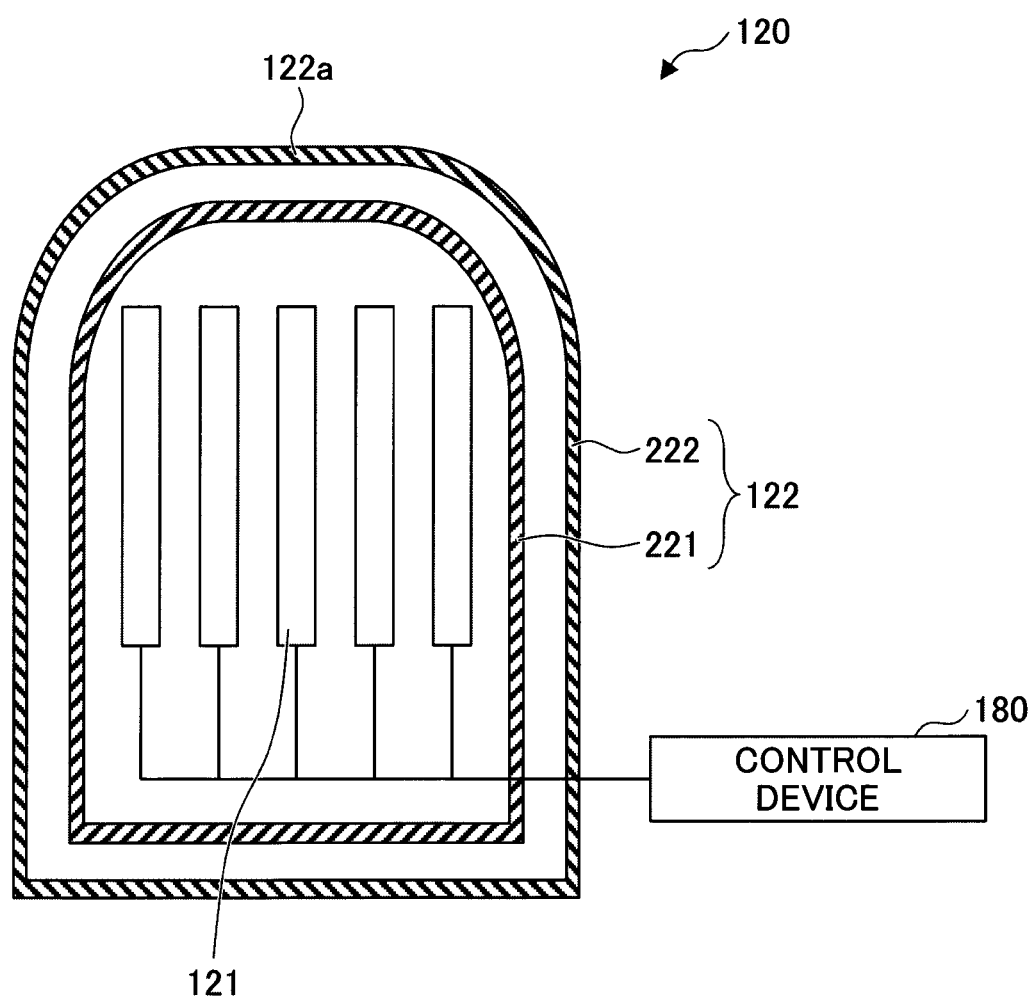

[Fig. 7]
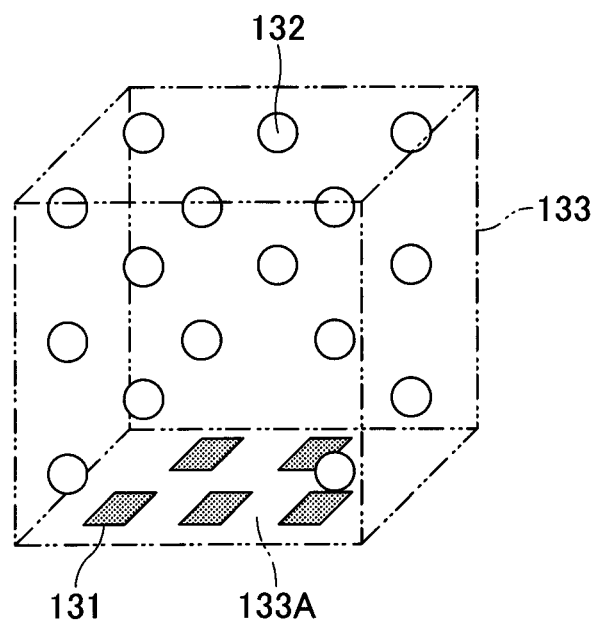
[Fig. 8A]
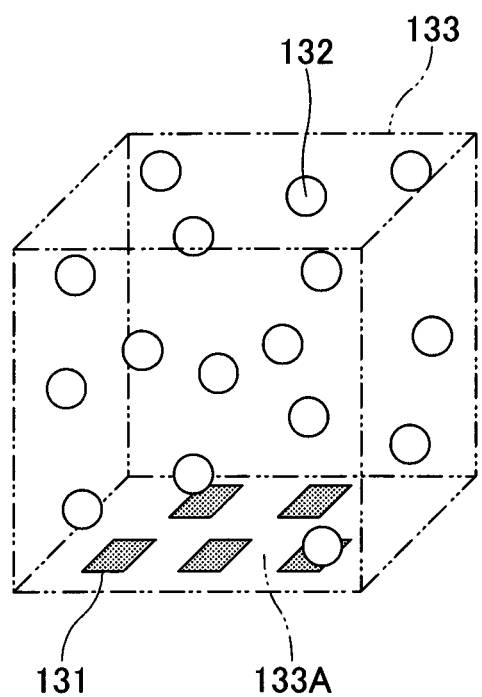

[Fig. 8B]
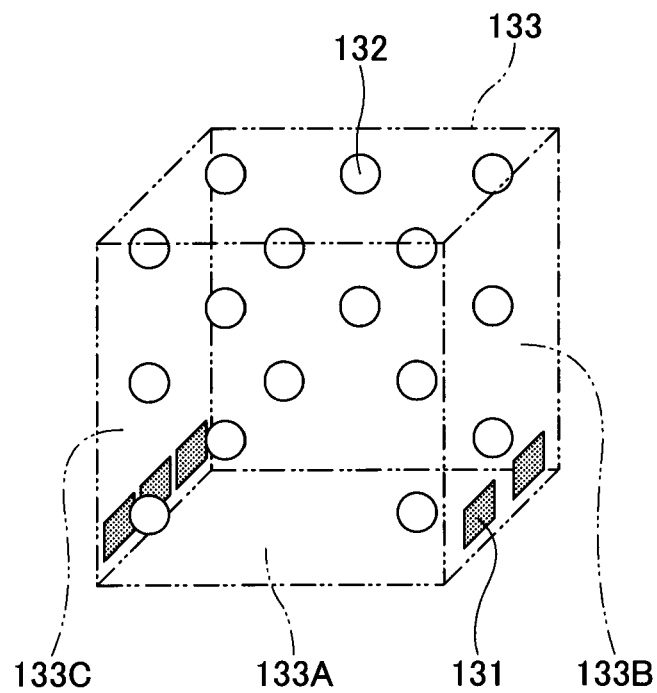
[Fig. 8C]
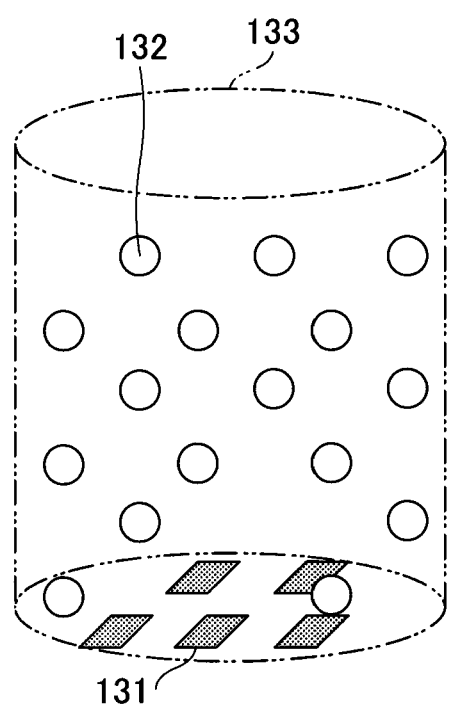

[Fig. 9]
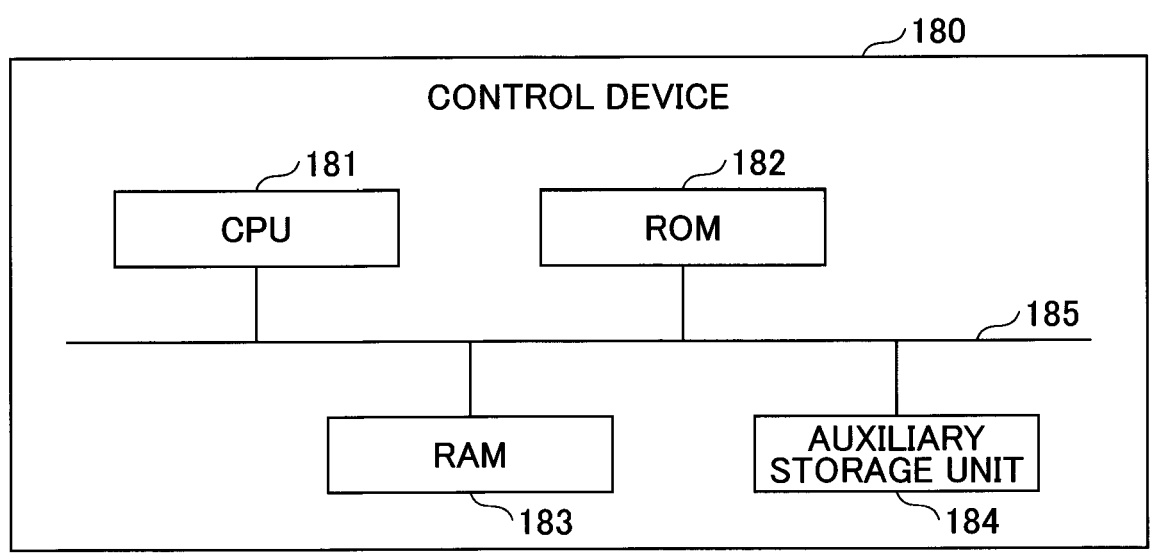

[Fig. 15]
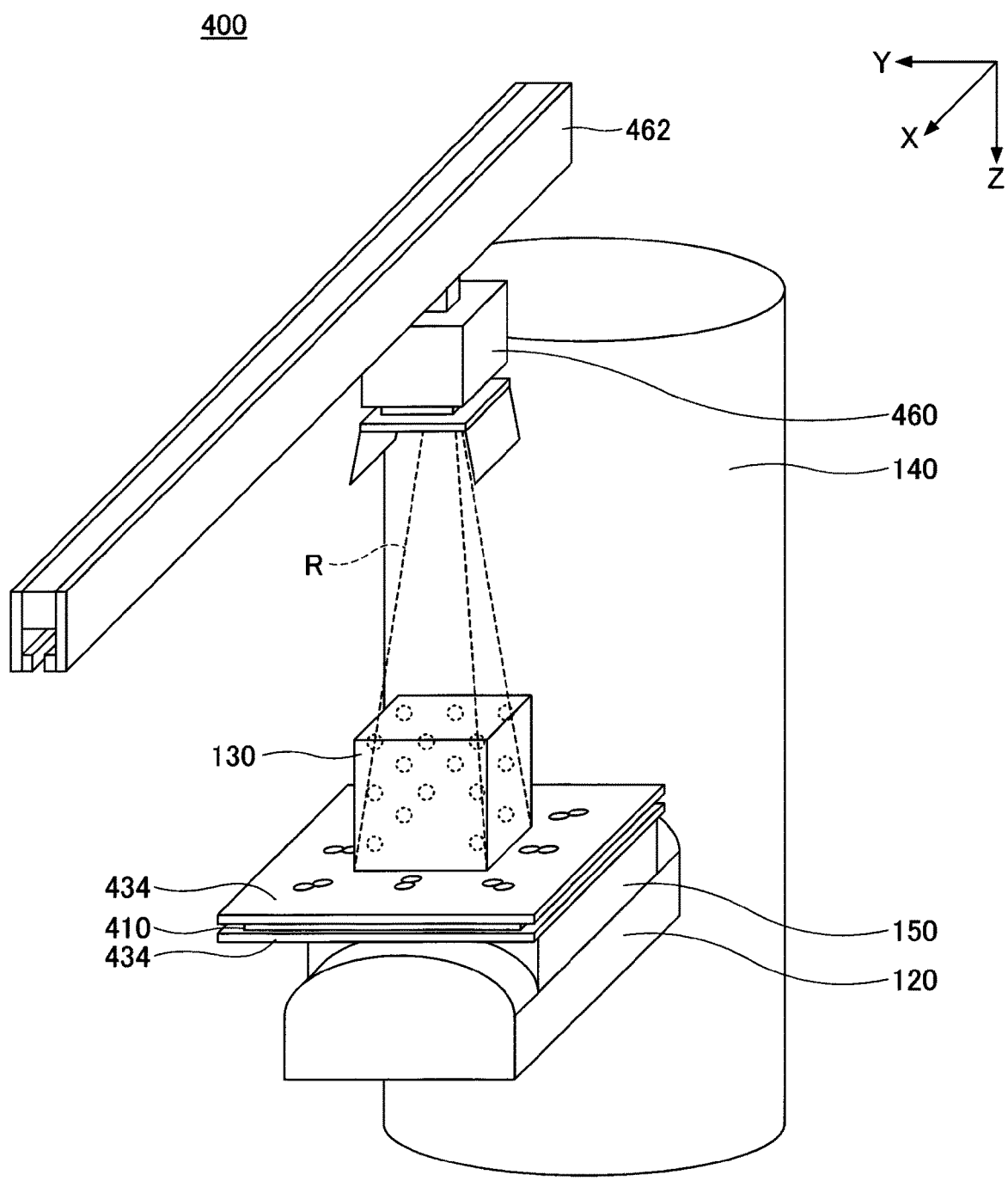

[Fig. 16]
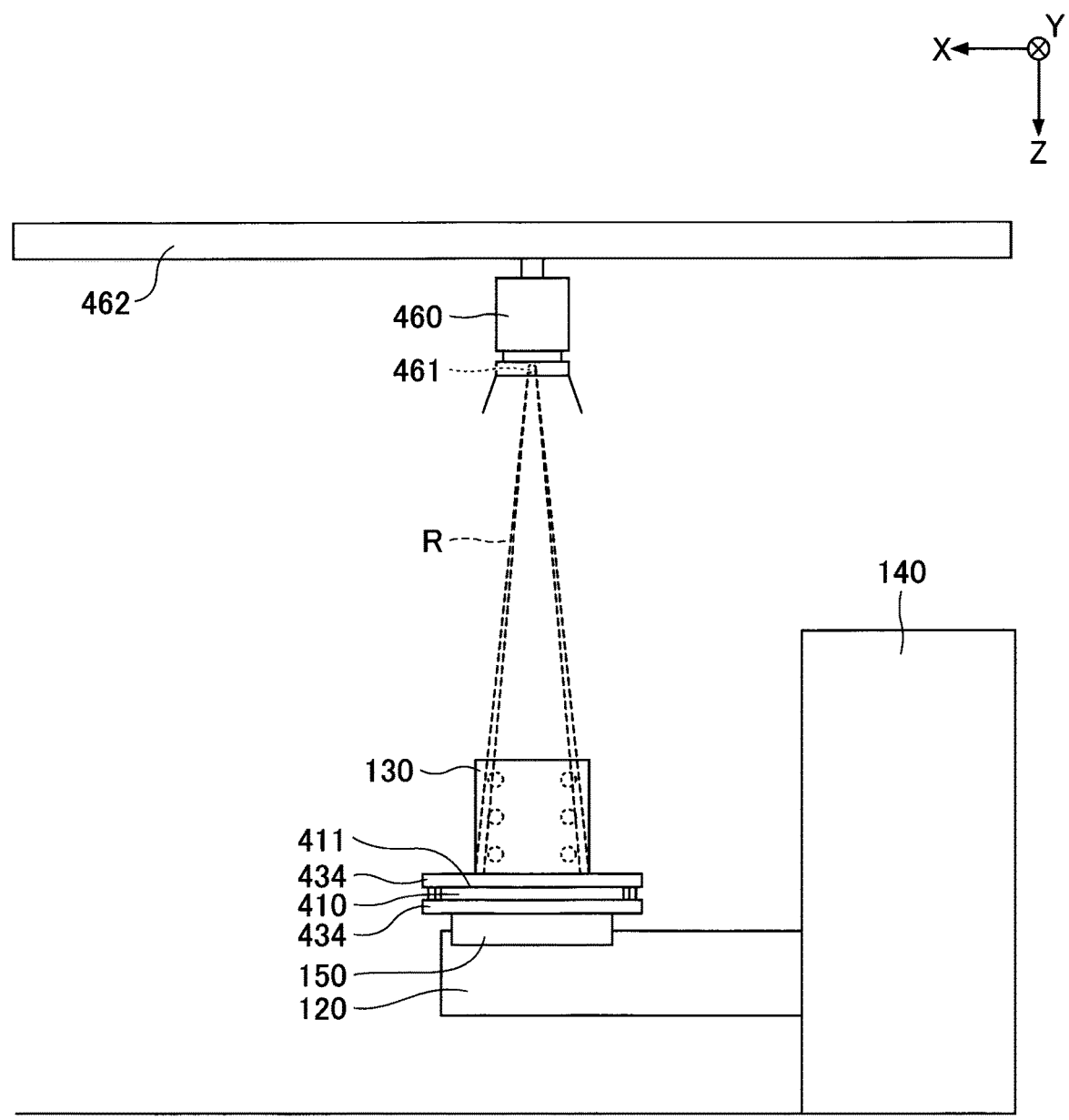

[Fig. 17]
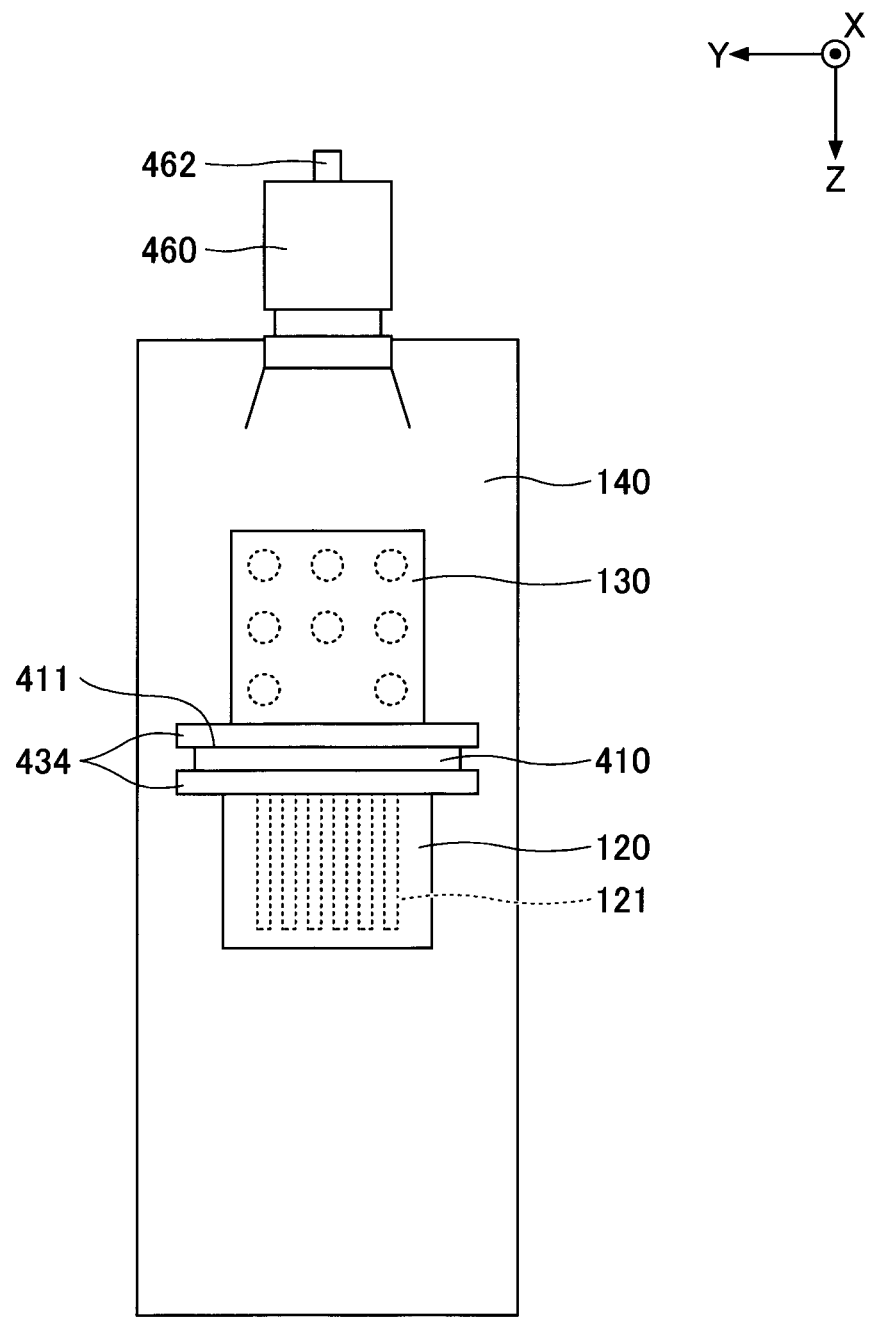

[Fig. 18]
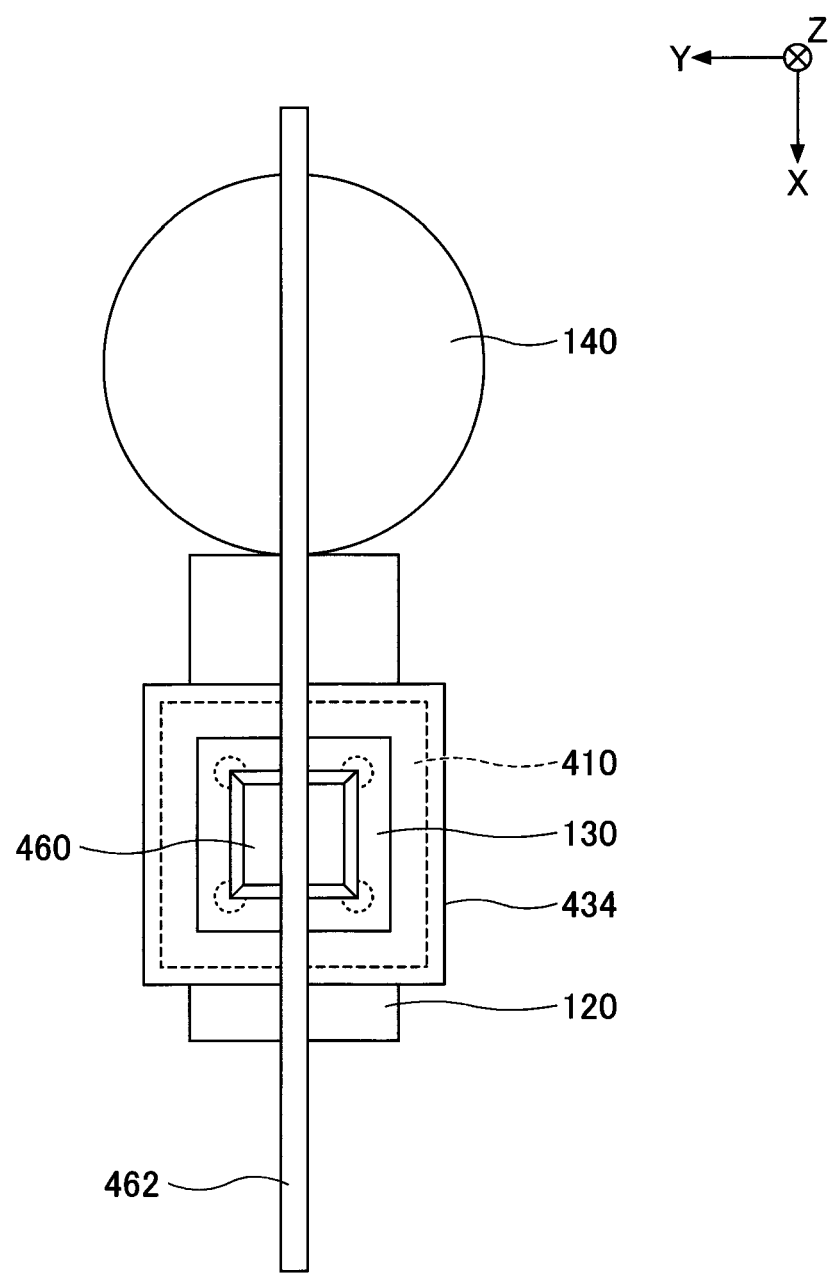

[Fig. 19]
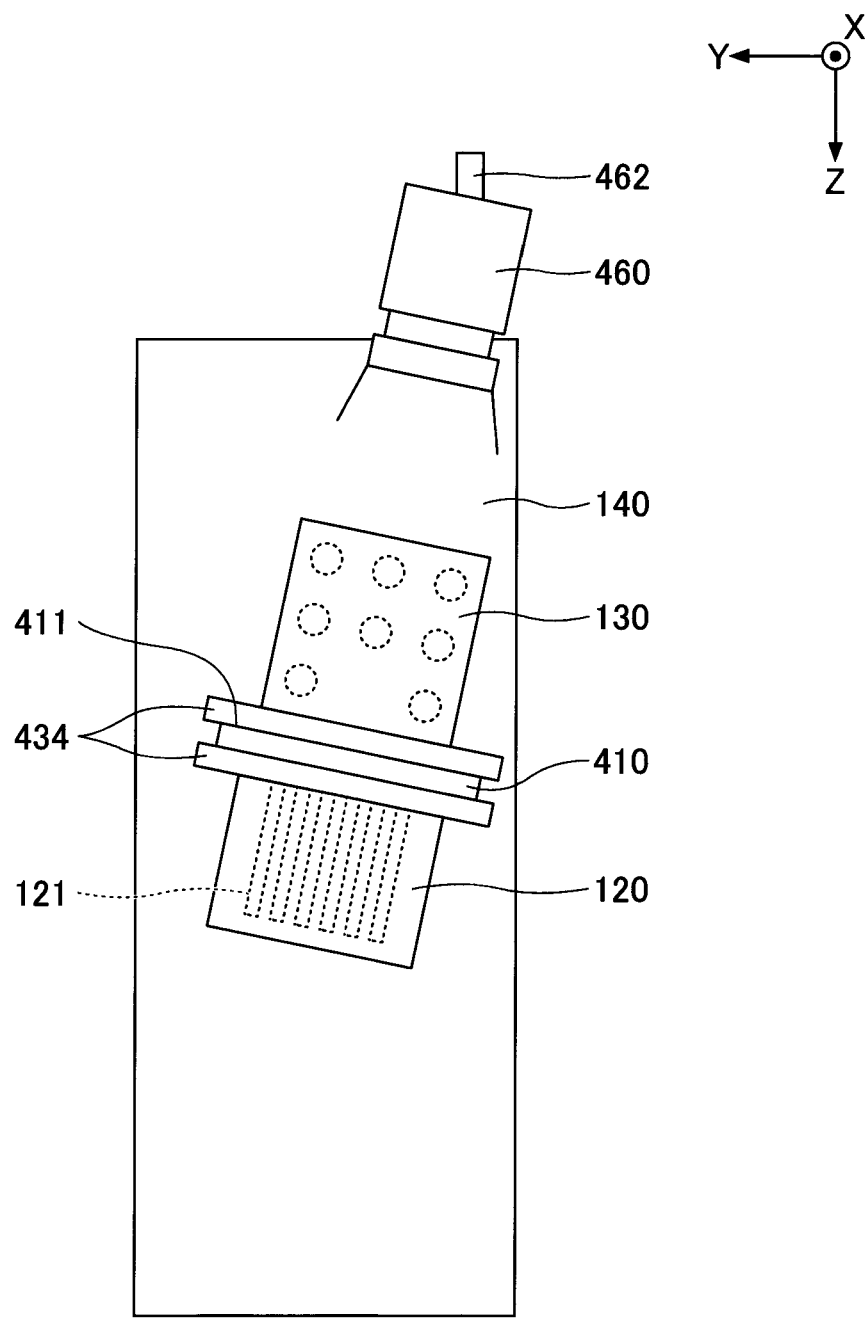

RADIATION SOURCE POSITION ESTIMATION SYSTEM, CALIBRATION SYSTEM AND BIOMAGNETIC MEASURING SYSTEM

TECHNICAL FIELD

The disclosures discussed herein relate to a radiation source position estimation system, a calibration system, and a biomagnetic measuring system.

BACKGROUND ART

Patent Document 1 proposes a device for measuring a position and a direction of a detection coil. Such a device is typically included in a superconducting quantum interference device sensor.

CITATION LIST

Patent Literature

[PTL 1] Japanese Unexamined Patent Application Publication No. H05-277082

SUMMARY OF INVENTION

Technical Problem

To detect biological magnetism of a subject by using a superconducting quantum interference device sensor, imaging of a subject is performed using radiation such as plain X-rays, and a sensing result of the biological magnetism of the subject is superimposed on an imaging result of the subject. The imaging result is affected by a position of a radiation source. Hence, a position of the radiation source is important. However, the technique disclosed in Patent Document 1 is unable to measure a position of the radiation source.

The present disclosure is intended to provide a radiation source position estimation system, a calibration system, and a biomagnetic measuring system, which are capable of accurately estimating a position of the radiation source.

Solution to Problem

According to one aspect of the present disclosure, a radiation source position estimation system is provided. The radiation source position estimation system includes a first position information specifier configured to specify position information of one or more elements included in a position measuring member, an imager configured to acquire images of the one or more elements formed by radiation emitted by a radiation source, and a second position information specifier configured to specify position information of the radiation source, based on the position information specified by the first position information specifier and the images acquired by the imager.

Advantageous Effect of the Invention

According to the present disclosure, it is possible to estimate a position of a radiation source with high accuracy.

BRIEF DESCRIPTION OF DRAWINGS

FIG. 4 is a front view illustrating a configuration of the biomagnetic measuring system according to the first embodiment;

FIG. 5 is a top view illustrating a configuration of the biomagnetic measuring system according to the first embodiment;

FIG. 6 is a cross-sectional view illustrating a configuration of a magnetic field measuring device;

FIG. 7 is a schematic view illustrating a configuration of a calibration tool;

FIG. 8A is a schematic view illustrating a configuration of a modified example of the calibration tool;

FIG. 8B is a schematic view illustrating a configuration of a modified example of the calibration tool;

FIG. 8C is a schematic view illustrating a configuration of a modified example of the calibration tool;

FIG. 9 is a diagram illustrating a configuration of a control device;

FIG. 15 is a perspective view illustrating a configuration of a biomagnetic measuring system according to a second embodiment;

FIG. 16 is a side view illustrating a configuration of the biomagnetic measuring system according to the second embodiment;

FIG. 17 is a front view illustrating a configuration of the biomagnetic measuring system according to the second embodiment;

FIG. 18 is a top view illustrating a configuration of the biomagnetic measuring system according to the second embodiment; and FIG. 19 is a front view illustrating a configuration of a biomagnetic measuring system according to a modification of the second embodiment.

DESCRIPTION OF EMBODIMENTS

Figure 1:
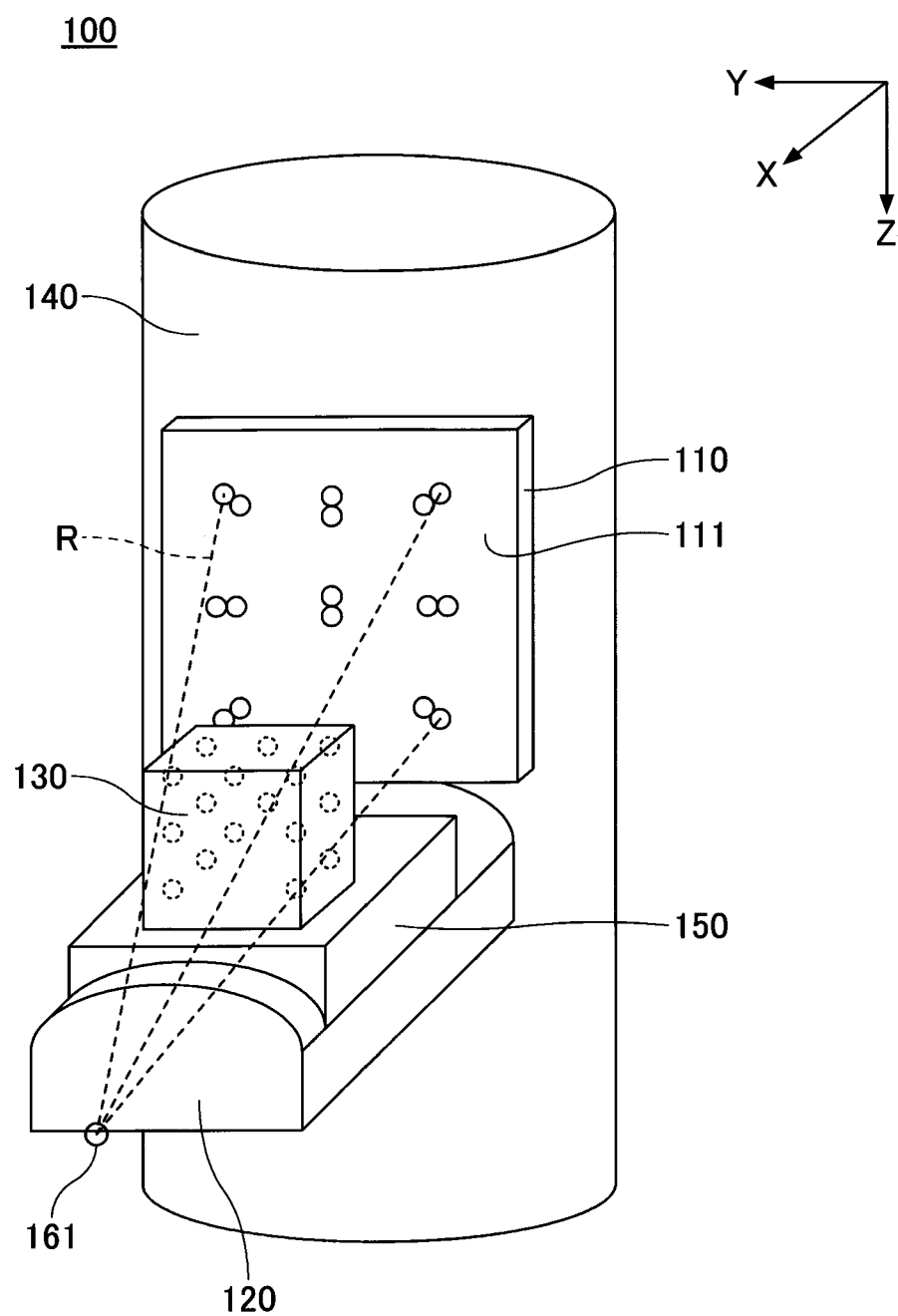
FIG. 1 is a perspective view (Part 1) illustrating a configuration of a biomagnetic measuring system according to a first embodiment.

Hereinafter, embodiments of the present disclosure will be described with reference to the accompanying drawings. In the present specification and the drawings, duplicated illustration will be omitted by assigning the same reference numerals to components having substantially the same functional configurations.

First Embodiment

<Overview of Biomagnetic Measuring System>

Figure 2:
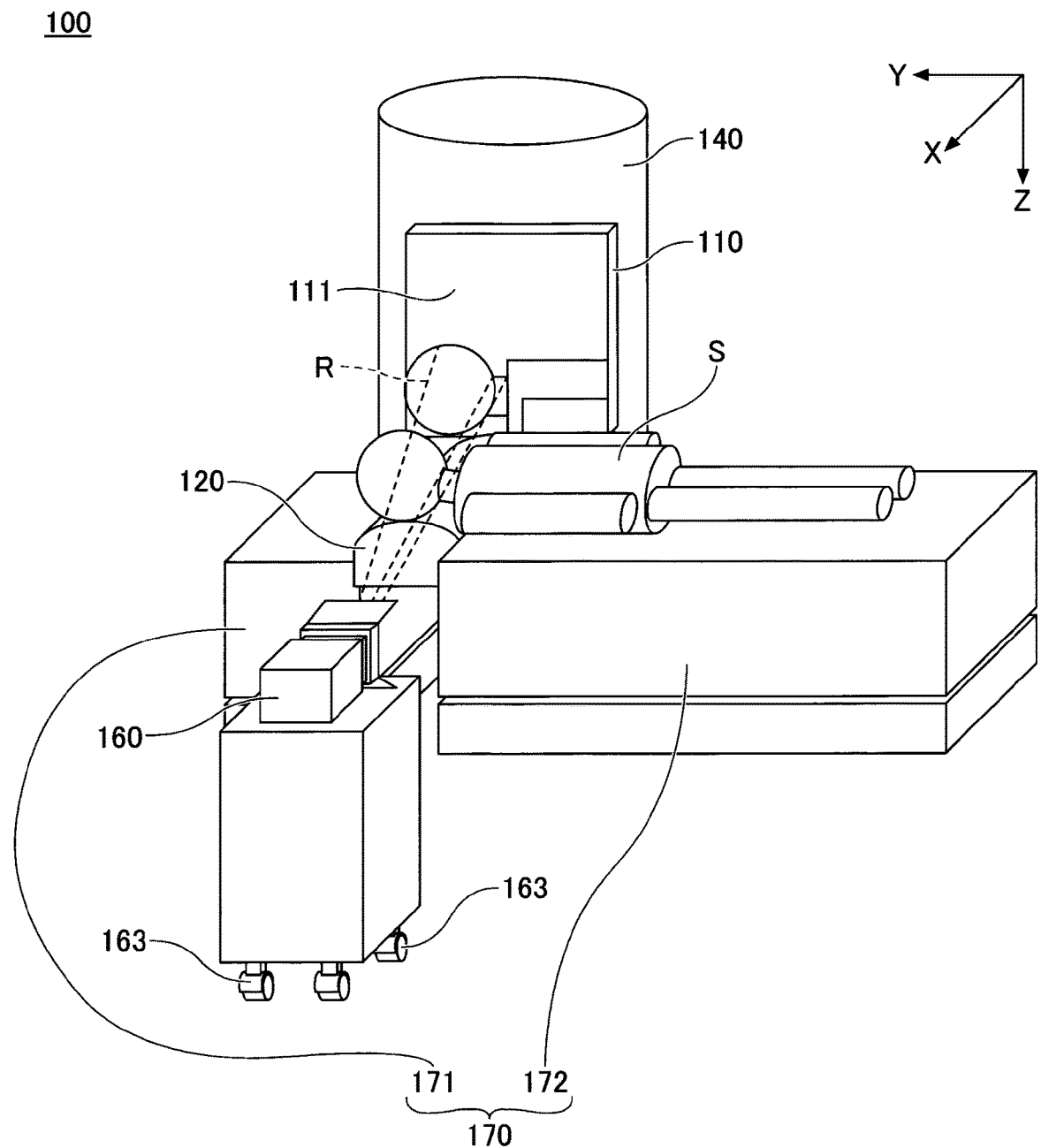
FIG. 2 is a perspective view (Part 2) illustrating a configuration of the biomagnetic measuring system according to the first embodiment.
Figure 3:
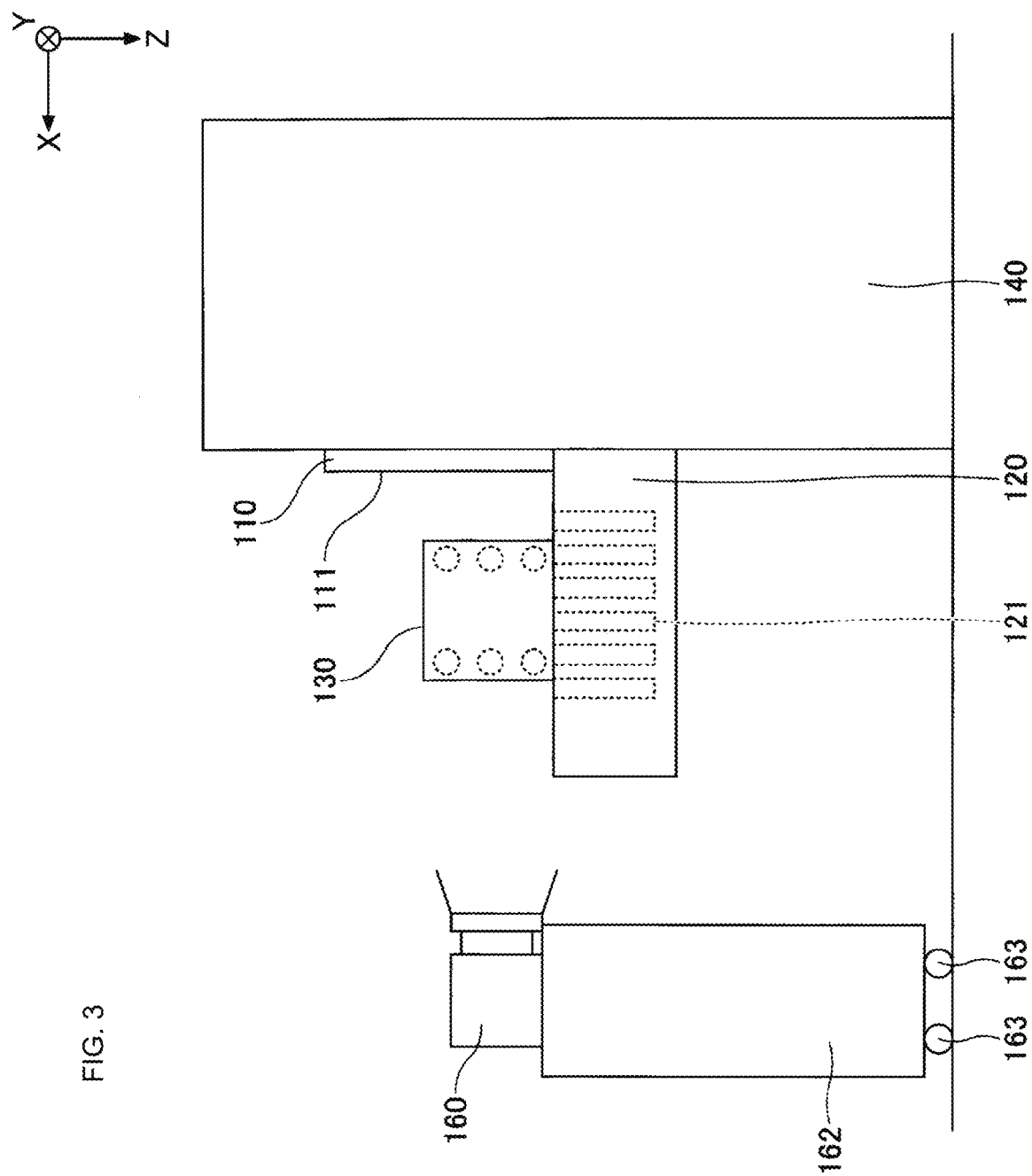
FIG. 3 is a side view illustrating a configuration of the biomagnetic measuring system according to the first embodiment.

In a biomagnetic measuring system according to a first embodiment, a radiation source and an imaging device are disposed along a substantially horizontal direction such that a magnetic field measuring device is interposed between the radiation source and the imaging device. When a subject is located in the biomagnetic measuring system, the subject is also interposed between the radiation source and the imaging device along a substantially horizontal direction. FIGS. 1 and 2 are perspective views illustrating a configuration of the biomagnetic measuring system according to the first embodiment. FIG. 1 illustrates a configuration upon estimating a position of a radiation source, and FIG. 2 illustrates a configuration upon biomagnetic measurement of the subject. FIG. 3 is a side view illustrating a configuration of the biomagnetic measuring system according to the first embodiment. FIG. 4 is a front view illustrating a configuration of the biomagnetic measuring system according to the first embodiment. FIG. 5 is a top view illustrating a configuration of the biomagnetic measuring system according to the first embodiment. FIGS. 3 to 5 illustrate a configuration upon estimating a position of the radiation source, similar to FIG. 1.

Figure 10:
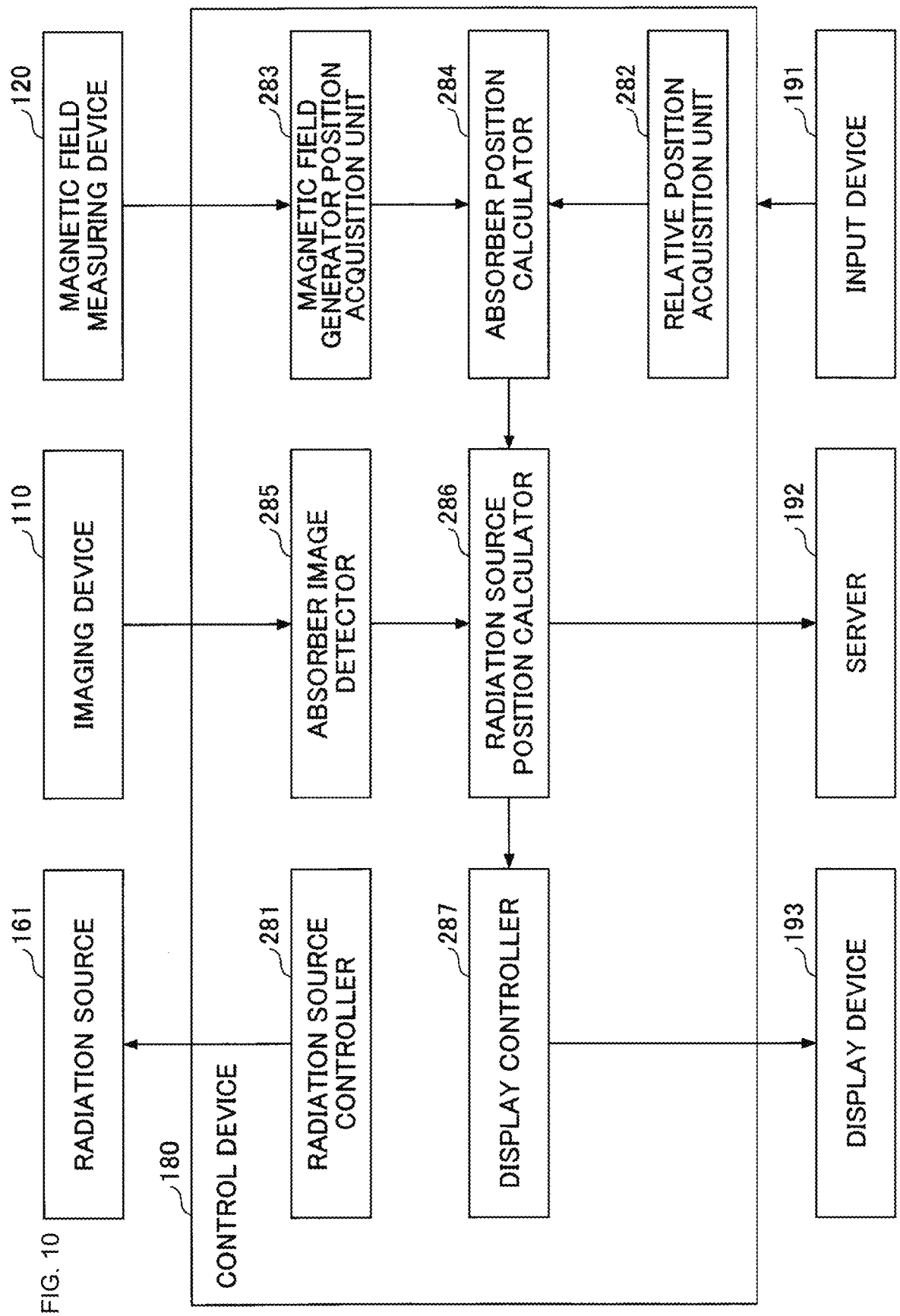
FIG. 10 is a diagram illustrating a functional configuration of a control device at time of estimating a position of a radiation source.

As illustrated in FIGS. 1 to 5, the biomagnetic measuring system 100 according to the first embodiment includes an imaging device 110, a magnetic field measuring device 120, a calibration tool 130, a support 140, a calibration tool stabilizer 150, a radiation exposure device 160 including a radiation source 161, a table 170, and a control device 180 (see FIG. 10, etc.). In the present specification and drawings, an X axis indicates a normal to an imaging surface 111 of the imaging device 110, and a Z axis indicates a vertically downward direction, and a Y axis indicates a direction orthogonal to the X axis and the Z axis in the right-handed system.

Imaging Device 110

The imaging device 110 is configured to acquire, as morphological images, digital image data of radiation R, which passes through a measuring area of a subject S or a calibration tool 130. Signals detected by the imaging device 110 are transmitted to the control device 180. The imaging device 110 also acquires a captured image of calibration tool 130. The imaging device 110 is an example of an imager.

The imaging device 110 may, for example, be a flat panel detector (hereinafter referred to as "FPD"). The FPD includes so-called "direct conversion system" and "indirect conversion system". In the direct conversion system, electric charges are generated by sensing elements according to a dose of applied radiation, and the generated electric charges are converted to electric signals. In the indirect conversion system, radiation applied is converted to electromagnetic waves with a different wavelength such as visible light by a scintillator or the like, electric charges are then generated by photoelectric conversion elements such as photodiodes according to energy of the converted electromagnetic waves, and the generated electric charges are converted to electric signals.

In addition, a so-called imaging plate (hereinafter, referred to as an IP) may be preferably used as the imaging device 110. The imaging plate is a film that is coated with photostimulable phosphor powder and housed in a cassette. Radiation R passing through the measurement area of the subject S is applied to the imaging plate, and radiation energy is stored in the photostimulable phosphor. The morphological images can then be acquired as digital image data by irradiating the imaging plate with laser light with a particular wavelength and scanning the irradiated laser with a scanner.

Magnetic Field Measuring Device 120

FIG. 6 is a cross-sectional view illustrating a configuration of the magnetic field measuring device 120. As illustrated in FIG. 6, the magnetic field measuring device 120 includes a magnetic sensor array having a plurality of magnetic sensors 121 configured to detect biological magnetism. The plurality of magnetic sensors 121 are held in a thermal insulated container 122 having a temperature control mechanism. The magnetic field measuring device 120 is an example of a detector.

(Magnetic Sensors 121)

The magnetic sensors 121 are each configured to detect biological magnetism generated from a subject S. Specifically, the magnetic sensors 121 each include a superconducting quantum interference device (SQUID) or an optical pumped atomic magnetometer (OPAM). These SQUID sensors and OPAM sensors have detection sensitivity sufficient to detect extremely weak biological magnetism on the order of $10^{-18}$ T. The magnetic sensors 121 are also configured to detect magnetic fields generated by the magnetic field generators 131 (see FIG. 7, etc.) included in the calibration tool 130.

The magnetic sensors 121 are typically arranged in a thermal insulated container 122 having a temperature control mechanism, as illustrated in FIG. 6. Signals from the respective magnetic sensors 121 are transmitted to a control device 180 for conversion to biomagnetic information. The plurality of magnetic sensors 121 not only provide a large amount of biomagnetic information, but also provide more detailed bioinformation by two-dimensional mapping of measured magnetic information or the like. Also, when the magnetic sensors 121 operate at room temperature, the temperature control mechanism and the thermal insulated container 122 are not required. The number and arrangement method of the magnetic sensors 121 are not particularly limited, and may be appropriately set according to the measurement region of the subject S.

(Temperature Control Mechanism)

The temperature control mechanism is a mechanism configured to adjust temperatures of the magnetic sensors 121 to predetermined temperatures suitable for operations of the magnetic sensors 121. The temperature control mechanism may be a known cooling or heating device. For example, if the magnetic sensors 121 are SQUID sensors, the magnetic sensors 121 operate at temperatures close to absolute zero in order to achieve a superconducting state. In this embodiment, the thermal insulated container 122 partially functions as the temperature control mechanism.

(Thermal Insulated Container 122)

As illustrated in FIG. 6, the thermal insulated container 122 is provided with an inner container 221 and an outer container 222, for example. The inner container 221 includes the plurality of magnetic sensors 121, and vacuum space is provided between the inner container 221 and the outer container 222. A coolant, such as liquid helium, is supplied to the inner container 221. Accordingly, the magnetic field measuring device 120 is controlled to a temperature suitable for operating the magnetic sensors 121.

The shape of the thermal insulated container 122 is not particularly specified, but the thermal insulated container 122 may preferably have a surface (hereinafter referred to as a facing surface 122a) shaping along a body surface of the measurement area of the subject S, where the facing surface 122a faces the subject S. The facing surface 122a is preferably planar or curved. For example, when the neck of the subject S is placed on the magnetic field measuring device 120 in order to perform the biomagnetic measurement, the facing surface 122a of the thermal insulated container 122 may preferably be curved along the arc of the cervical spinal cord.

The thermal insulated container 122 is not limited to the vacuum thermal insulated container as illustrated in FIG. 6. The thermal insulated container 122 may be made of foam or the like. The thermal insulated container 122 is preferably made of a nonmagnetic material with low magnetic permeability. The use of the thermal insulated container 122 made of a non-magnetic material can prevent adverse effects, which are caused by fluctuations in the environmental magnetism, on the magnetic sensors 121 while the thermal insulated container 122 vibrates. Examples of non-magnetic materials include plastic materials such as acrylic resins; inorganic materials such as silica and alumina; non-ferrous metals such as copper, brass, aluminum and titanium; and mixtures of these materials.

Calibration Tool 130

The calibration tool 130 is disposed above the magnetic field measuring device 120 when estimating a position of the radiation source included in the radiation exposure device 160. FIG. 7 is a schematic view illustrating a configuration of the calibration tool 130. As illustrated in FIG. 7, the calibration tool 130 includes a plurality of magnetic field generators 131 configured to generate magnetic fields, a plurality of absorbers 132 configured to absorb radiation emitted by the radiation source 161, and a support 133 configured to support the magnetic field generators 131 and the absorbers 132. The magnetic field generators 131 are each, for example, a coil configured to receive electric current supplied. The absorbers 132 are each, for example, a sphere made of iron or made of metal having density higher than iron such as tungsten. The absorbers 132 may have a shape such as a cylinder other than a sphere. The support 133 is configured to let through radiation more than the absorbers 132 let through, upon receiving the radiation emitted by the radiation source 161. The support 133 is, for example, made of plastic.

As illustrated in FIG. 7, the outer shape of the support 133 is substantially rectangular. For example, one face 133A is provided with a plurality of magnetic field generators 131, and a plurality of absorbers 132 is disposed at positions distanced from the face 133A. For example, as illustrated in FIG. 8A, the absorbers 132 may be disposed in an irregular manner, or as illustrated in FIG. 8B, the magnetic field generators 131 may be disposed on separate faces 133B and 133C at positions close to the face 133A, where the faces 133B and 133C face each other. Further, as illustrated in FIG. 8C, the outer shape of the support 133 may be substantially cylindrical. The calibration tool 130 is an example of a position measuring member. The absorbers 132 are each an example of an element.

Support 140

The support 140 is, for example, a cylinder. The magnetic field measuring device 120 is fixed to the support 140. The imaging device 110 is removably disposed on the support 140.

Calibration Tool Stabilizer 150

The calibration tool stabilizer 150 is configured to stabilize a position of the calibration tool 130 on the magnetic field measuring device 120. That is, the calibration tool stabilizer 150 prevents misalignment and wobbles of the calibration tool 130. An example of the calibration tool stabilizer 150 may include a non-skid pad. As the calibration tool stabilizer 150, a structure, which has a flat face facing the calibration tool 130 and a face along the facing surface 122a of the magnetic field measuring device 120, may be used. The calibration tool stabilizer 150 is not necessarily required when misalignment and wobbles of the calibration tool 130 are unlikely to occur. Illustration of the calibration tool stabilizer 150 is omitted from FIGS. 3 to 5.

Radiation Exposure Device 160

The radiation exposure device 160 includes a radiation source 161. The radiation source 161 may be any known radiation source configured to apply radiation to a living body. In the present invention, "radiation" not only indicates commonly used plain X-rays, but also indicates a broader concept of radiation. Examples of such radiation may include beams made of particles (including photons) such as α-rays, β-rays, and γ-rays, which are released due to radioactive decay; and beams having the same or higher energy level than plain X-rays such as particle rays and cosmic rays. In view of the high versatility, the plain X-rays may preferably be used as radiation.

The radiation exposure device 160 is, for example, disposed on a movable carriage 162 provided with casters 163 in order to facilitate the movement of the radiation exposure device 160. The movable carriage 162 may preferably have a lifting mechanism configured to adjust the height of a surface on which the radiation exposure device 160 is placed. The movable carriage 162 may have the ability to switch between locking and unlocking of the casters 163. Without considering the movement facilitation of the radiation exposure device 160, the movable carriage 162 may not necessarily be provided with casters 163. As materials of the movable carriage 162, metal that can withstand the weight of the radiation exposure device 160 may be used.

(Table 170)

The table 170 is not particularly specified in shape insofar as the table 170 on which the subject S is placed can support the subject S; however, as illustrated in FIG. 2, the table 170 may be formed by a plurality of section-separated tables, such as a head table 171 for supporting the head of the subject S and a body table 172 for supporting the body of the subject S. The magnetic field measuring device 120 may be disposed between the head table 171 and the body table 172 so as to face a measurement area of the subject S.

It is preferable that those members forming the table 170 should be made of a nonmagnetic material having low magnetic permeability. The table 170 made of a nonmagnetic material may be able to prevent adverse effects caused by fluctuations of environmental magnetism on the magnetic sensors 121 even when the subject S vibrates. As with the thermal insulated container 122, non-magnetic materials to be used for the members forming the table 170 include plastic materials such as acrylic resin; inorganic materials such as silica and alumina; non-ferrous metals such as copper, brass, aluminum and titanium; and mixtures of these materials. The table 170 is required to have load resistance, impact resistance, and the like in order to support part of or all of the subject S. Thus, it is preferable that the table 170 should be made of metal parts with high mechanical strength or engineering plastic.

Control Device 180

The control device 180 includes a CPU (Central Processing Unit) 181, a ROM (Read Only Memory) 182, a RAM (Random Access Memory) 183, and an auxiliary storage unit 184, as illustrated in FIG. 9. The CPU 181, the ROM 182, the RAM 183, and the auxiliary storage unit 184 constitute a so-called computer. These components of the control device 180 are interconnected via a bus 185.

The CPU 181 is configured to execute various programs (e.g., a program for estimating a position of a radiation source) stored in the auxiliary storage unit 184.

The ROM 182 is a non-volatile primary storage device. The ROM 182 stores various programs, data and the like, which are necessary for causing the CPU 181 to execute various programs stored in the auxiliary storage unit 184. Specifically, the ROM 182 stores boot programs such as BIOS (Basic Input/Output System) and EFI (Extensible Firmware Interface).

The RAM 183 is a volatile primary storage device such as a DRAM (Dynamic Random Access Memory) or an SRAM (Static Random Access Memory). The RAM 183 functions as a work area for loading programs upon various programs stored in the auxiliary storage unit 184 being executed by the CPU 181.

The auxiliary storage unit 184 is an auxiliary storage device. The auxiliary storage unit 184 stores various programs executed by the CPU 181 and various data generated upon various programs being executed by the CPU 181.

<Functional Configuration of Control Device 180 at Time of Estimating a Position of the Radiation Source 161>

As illustrated in FIG. 10, at time of estimating a position of the radiation source 161, the control device 180 functionally includes a radiation source controller 281, a relative position acquisition unit 282, a magnetic field generator position acquisition unit 283, an absorber position calculator 284, an absorber image detector 285, a radiation source position calculator 286, and a display controller 287.

(Radiation Source Controller 281)

The radiation source controller 281 is configured to control a timing of radiation emission performed by the radiation source 161.

(Relative Position Acquisition Unit 282)

The relative position acquisition unit 282 is configured to acquire relative position relationships between the magnetic field generators 131 and the absorbers 132 within the calibration tool 130. The relative position acquisition unit 282 acquires relative position relationships from, for example, design values of the calibration tool 130. The relative position acquisition unit 282 may, for example, acquire relative position relationships between the magnetic field generators 131 and the absorbers 132, based on measurements of the internal structure of the completed calibration tool 130.

(Magnetic Field Generator Position Acquisition Unit 283)

The magnetic field generator position acquisition unit 283 is configured to receive signals output from the magnetic sensors 121 of the magnetic field measuring device 120 and acquire positions of the magnetic field generators 131 included in the calibration tool 130.

(Absorber Position Calculator 284)

The absorber position calculator 284 is configured to compare respective positions of the magnetic field generators 131 acquired by the magnetic field generator position acquisition unit 283 and relative positions acquired by the relative position acquisition unit 282, and to calculate positions of the absorbers 132. The absorber position calculator 284 may use the ICP (iterative close point) algorithm to calculate the positions of the absorbers 132. The absorber position calculator 284 is an example of a first position information specifier.

(Absorber Image Detector 285)

The absorber image detector 285 is configured to detect images of the absorbers 132 from a captured image, which is output from the imaging device 110. When the absorbers 132 each have a spherical shape, images of the absorbers 132 in the captured image are circles. In this case, the absorber image detector 285 performs circle detection to detect all the circle images of the absorbers 132 in the captured image, and to acquire positions of the absorbers 132 from the centers of respective circle images. The Hough transform may be used for circle detection. The absorber image detector 285 is an example of an image detector.

(Radiation Source Position Calculator 286)

The radiation source position calculator 286 is configured to calculate a position of the radiation source 161 using the positions of the absorbers 132 calculated by the absorber position calculator 284 and the positions of the absorbers 132 detected by the absorber image detector 285. A method of calculating a position of the radiation source 161 will be described in detail below. The radiation source position calculator 286 outputs a calculated position of the radiation source 161 to a server 192 and delivers the calculated position of the radiation source 161 to the display controller 287. The server 192 stores the position of the radiation source 161. The radiation source position calculator 286 is an example of a second position information specifier.

(Display Controller 287)

The display controller 287 is configured to display on the display device 193 a position of the radiation source 161 calculated by the radiation source position calculator 286.

<Method of Estimating a Position of Radiation Source 161>

Figure 11:
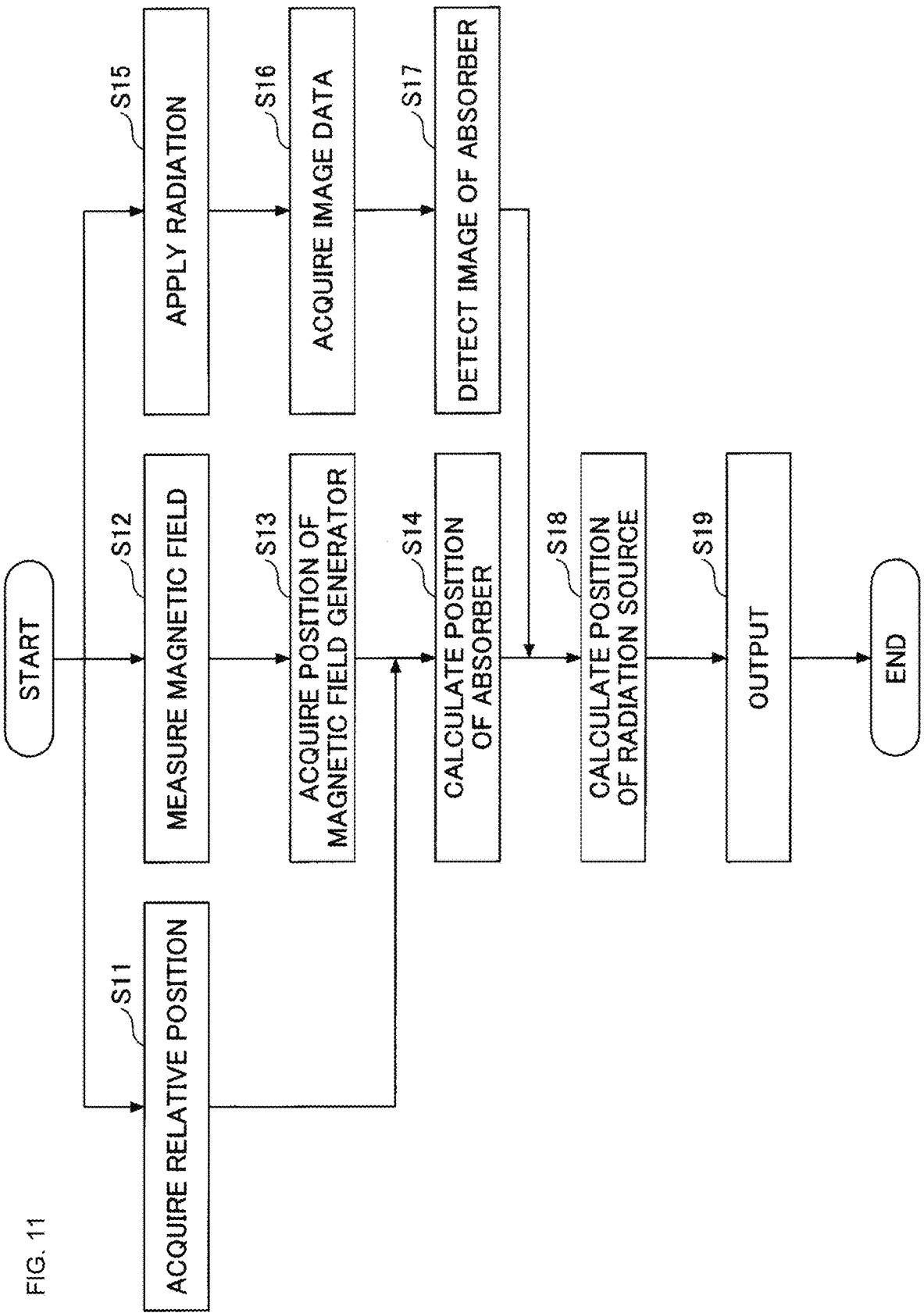
FIG. 11 is a flowchart illustrating a method of estimating a position of a radiation source.

Next, a method of estimating a position of the radiation source 161 will be described. To estimate a position of the radiation source 161, a calibration tool 130 is disposed between the radiation exposure device 160 and the imaging device 110, and a magnetic field measuring device 120 is disposed beneath the calibration tool 130. The calibration tool 130 is disposed such that magnetic fields generated by the magnetic field generators 131 are measured by the magnetic field measuring device 120, and the absorbers 132 are displayed on the imaging surface 111. For example, in a case where a distance from the radiation source 161 to the imaging surface 111 is 1500 mm, a diameter of each absorber 132 is 1.2 mm, a Z-axis dimension of the imaging surface 111 is 290.4 mm, a Y-axis dimension of the imaging surface 111 is 176.4 mm, and intervals between the absorbers 132 are each 100 mm, the calibration tool 130 is preferably disposed at a position 450 mm to 1450 mm distanced from the radiation source 161. This arrangement is preferable because the absorbers 132 are prevented from being superimposed on each other on the imaging surface 111. FIG. 11 is a flowchart illustrating a method of estimating a position of the radiation source 161.

First, in step S11, the relative position acquisition unit 282 acquires relative positions between the magnetic field generators 131 and the absorbers 132 included in the calibration tool 130.

Also, the magnetic field generators 131 are caused to generate magnetic fields, and the magnetic field measuring device 120 measures the magnetic fields generated by the magnetic field generators 131 (step S12). Subsequently, in step S13, the magnetic field generator position acquisition unit 283 receives signals output from the magnetic sensors 121 of the magnetic field measuring device 120, and acquires positions of the magnetic field generators 131 included in the calibration tool 130. Thereafter, in step S14, the absorber position calculator 284 compares positions of the magnetic field generators 131 acquired by the magnetic field generator position acquisition unit 283 and the relative positions acquired by the relative position acquisition unit 282 to calculate positions of the absorbers 132.

Also, the radiation source 161 applies radiation to the calibration tool 130, based on the control of the radiation source 161 performed by the radiation source controller 281 (step S15). The imaging device 110 then acquires image data from the radiation, which has passed through the calibration tool 130 (step S16). A portion of the radiation applied to the calibration tool 130 passes through the support 133, and another portion of radiation applied to the calibration tool 130 is absorbed by the absorbers 132. Accordingly, shadows of the absorbers 132 are displayed as respective images on the imaging surface 111 of the imaging device 110. The image data thus includes the images of the absorbers 132. Then, in step S17, the absorber image detector 285 detects the images of the absorbers 132 from the image data.

Subsequently, the radiation source position calculator 286 calculates a position of the radiation source 161 using the positions of the absorbers 132 calculated by the absorber position calculator 284 and the positions of the absorbers 132 detected by the absorber image detector 285 (step S18).

Figure 12:
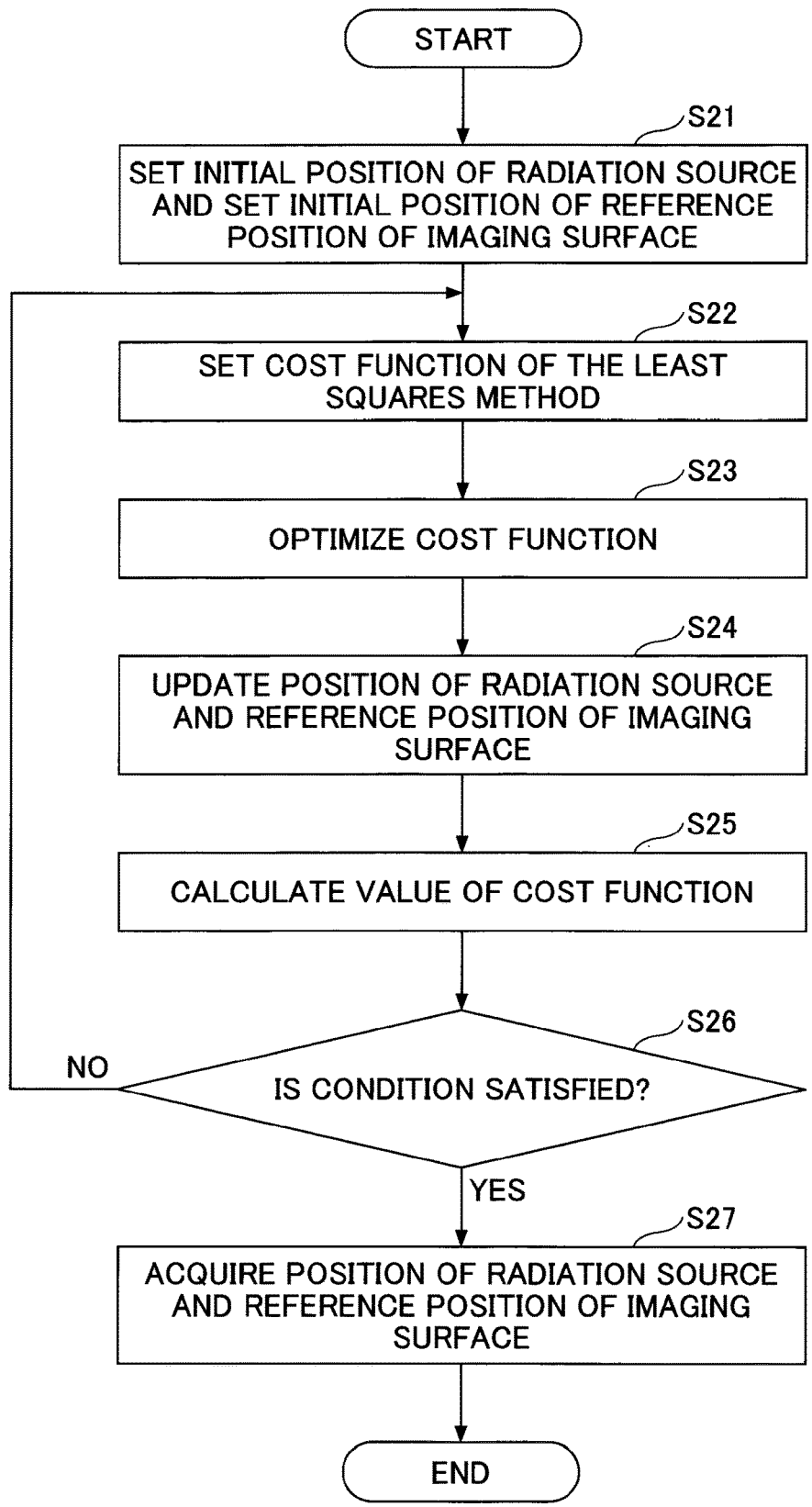
FIG. 12 is a flowchart illustrating a method of calculating a position of a radiation source.

Herein, a method of calculating a position of the radiation source 161 will be described. FIG. 12 is a flowchart illustrating a method of calculating a position of the radiation source 161. Hereinafter, coordinates of a position of each absorber 132 calculated by the absorber position calculator 284 are referred to as "subject coordinates", and coordinates of a position of each absorber 132 detected by the absorber image detector 285 are referred to as "projection coordinates".

First, for each of a plurality of subject coordinates, the radiation source position calculator 286 calculates the center of gravity of subject coordinates. The radiation source position calculator 286 sets an initial position of the radiation source at a given position on a positive side of the X axis on a straight line that passes through the center of gravity of the subject coordinates. The radiation source position calculator 286 sets a reference point of projection coordinates at the center of gravity of the projection coordinates. The radiation source position calculator 286 sets an initial position of the projection coordinates at a given position on a negative side of the X axis on the straight line that passes through the reference point of the projection coordinates and the center of gravity of the subject coordinates (step S21).

Subsequently, the radiation source position calculator 286 sets a cost function of the least squares method (step S22). That is, the radiation source position calculator 286 sets a cost function so as to minimize a distance between an intersection position of each of the subject coordinates intersecting the imaging surface 111 and a position of a counterpart one of the projection coordinates. Note that the intersection position of each of the subject coordinates intersecting the imaging surface 111 is a position at which a straight line extending from the radiation source 161 passes through the corresponding subject coordinates and intersects the imaging surface 111.

The following illustrates a cost function. For example, assuming that position coordinates of the radiation source 161 are (x0, y0, z0), reference coordinates of the projection coordinates are (xb1, yb1, zb1), the i-th projection coordinates with respect to the reference coordinates are (ni, li, mi), and the slope of the imaging surface is (θ, φ, ψ). When the slope of the imaging surface is (θ, φ, ψ), the rotation matrix is expressed by Math. 1.

$$\begin{pmatrix} \cos(\psi)\cos(\theta) & \sin(\phi)\sin(\psi)\cos(\theta) - \cos(\phi)\sin(\theta) & \sin(\phi)\sin(\theta) + \cos(\phi)\sin(\psi)\cos(\theta) \\ \cos(\psi)\sin(\theta) & \sin(\phi)\sin(\psi)\sin(\theta) + \cos(\phi)\cos(\theta) & \cos(\phi)\sin(\psi)\sin(\theta) - \sin(\phi)\cos(\theta) \\ -\sin(\psi) & \sin(\phi)\cos(\psi) & \cos(\phi)\cos(\psi) \end{pmatrix} \quad [\text{Math. 1}]$$

Accordingly, the i-th projection coordinates with respect to the reference coordinates are rotated by (θ, φ, ψ) about the X axis, the Y axis, and the Z axis, so that i-th projection coordinates are moved to coordinates (xt, yt, zt) represented by Math. 2, where the i-th projection coordinates are moved with respect to the reference coordinates of the projection coordinates, which are used as a reference position.

$$\begin{pmatrix} xt \\ yt \\ zt \end{pmatrix} = \begin{pmatrix} \cos(\psi)\cos(\theta) & \sin(\phi)\sin(\psi)\cos(\theta) - \cos(\phi)\sin(\theta) & \sin(\phi)\sin(\theta) + \cos(\phi)\sin(\psi)\cos(\theta) \\ \cos(\psi)\sin(\theta) & \sin(\phi)\sin(\psi)\sin(\theta) + \cos(\phi)\cos(\theta) & \cos(\phi)\sin(\psi)\sin(\theta) - \sin(\phi)\cos(\theta) \\ -\sin(\psi) & \sin(\phi)\cos(\psi) & \cos(\phi)\cos(\psi) \end{pmatrix} \begin{pmatrix} n1 \\ l1 \\ m1 \end{pmatrix} + \begin{pmatrix} xb1 \\ yb1 \\ zb1 \end{pmatrix} \quad [\text{Math. 2}]$$

Further, a plane is represented by Math. 3 using a point (xd, yd, zd) on the plane and the normal vector (a, b, c) to the plane.

$$c(z - zd) + b(y - yd) + a(x - xd) = 0 \quad [\text{Math. 3}]$$

Accordingly, assuming that the imaging surface 111 is oriented along the X axis at an initial state, a normal vector to the imaging surface 111 is (1, 0, 0), and the imaging surface 111 is represented by Math. 4 using the reference point of the projection coordinates and the normal vector.

$$-\sin(\psi)(z - zb1) + \cos(\psi)\sin(\theta)(y - yb1) + \cos(\psi)\cos(\theta)(x - xb1) = 0 \quad [\text{Math. 4}]$$

Further, assuming that the i-th subject coordinates are (xai, yai, zai), a straight line connecting the radiation source 161 and the i-th subject coordinates is represented by Math. 5.

$$\frac{x - xa_1}{xa_1 - x0} = \frac{y - ya_1}{ya_1 - y0} = \frac{z - za_1}{za_1 - z0} \quad [\text{Math. 5}]$$

Accordingly, coordinates (xp, yp, zp) at an intersection of the plane represented by Math. 4 and the straight line represented by Math. 5 can be obtained. Then, a value D of the square of the three-dimensional Euclidean distance between the projection coordinates (xt, yt, zt) and the coordinates (xp, yp, zp) at the intersection of the imaging surface 111 and the straight line is represented by Math. 6.

$$D = (zt - zp)^2 + (yt - yp)^2 + (xt - xp)^2 \quad [\text{Math. 6}]$$

The value D of Math. 6 is calculated for each of the absorbers 132, and the sum of these values D results in a cost function.

After setting the cost function in step S22, the radiation source position calculator 286 optimizes the cost function (step S23). In cost function optimization, the radiation source position calculator 286 differentiates the cost function set in step S22 with respect to unknowns. When the above-described cost function is used, derivatives of the cost function are obtained with respect to nine parameters x0, y0, z0, xb1, yb1, zb1, θ, φ, and ψ, which are unknowns.

Subsequently, the radiation source position calculator 286 updates the position of the radiation source 161 and the reference position of the imaging surface 111 to optimized positions obtained by the optimization (step S24). Thereafter, the radiation source position calculator 286 calculates updated values of the cost function (step S25). The radiation source position calculator 286 repeatedly performs the processing of step S22 to S25, and determines, upon predetermined conditions being satisfied, values of the above-described nine parameters (x0, y0, z0, xb1, yb1, zb1, θ, φ, and ψ) at the time of the predetermined conditions being satisfied (step S26). The radiation source position calculator 286 then acquires the position of the radiation source 161, the reference position of the imaging surface 111, and the slope of the imaging surface 111 (step S27). Note that thresholds may be set in advance for the updated values of the cost function, and the repeated processing may be terminated when the values of the cost function are less than the preset thresholds. Optimization may be performed using Adam (Adaptive Moment Estimation), which is a gradient descent method.

The position of the radiation source 161 is calculated in this manner (step S18).

Thereafter, the radiation source position calculator 286 outputs, to the server 192, the values of the above-described nine parameters (x0, y0, z0, xb1, yb1, zb1, θ, φ, and ψ) including parameters indicating the position of the radiation source 161, and delivers these values to the display controller 287. The display controller 287 displays the position of the radiation source 161 calculated by the radiation source position calculator 286 on the display device 193.

The position of the radiation source 161 can be estimated in this manner. That is, the biomagnetic measuring system 100 partially functions as a radiation source position estimation system, which is configured to estimate a position of the radiation source 161.

Figure 13:
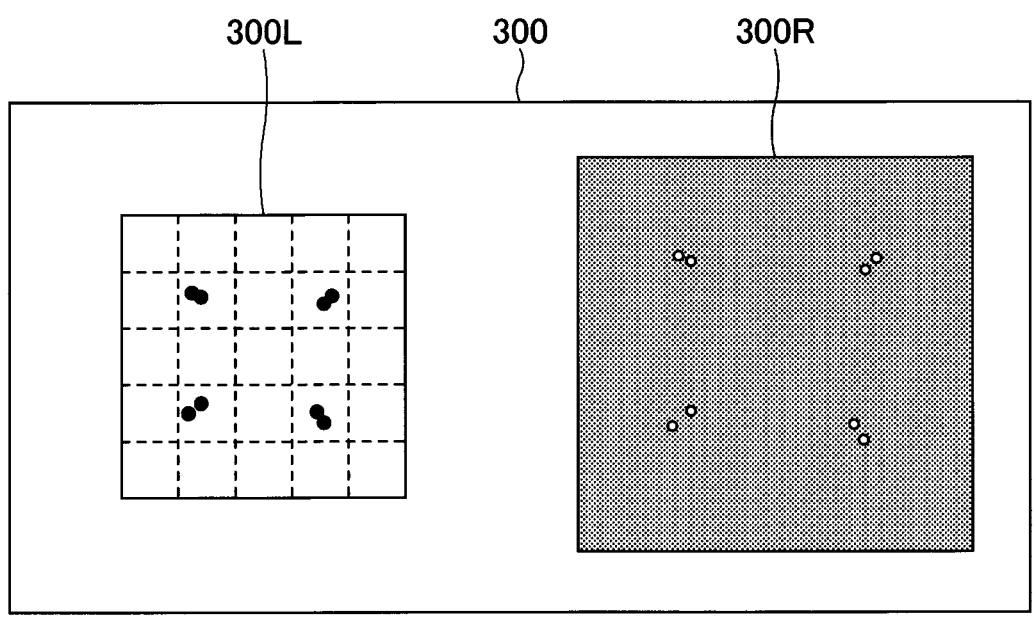
FIG. 13 is a schematic view illustrating an example of a display.

The display controller 287 may display, on the display device 193, position coordinates of the magnetic field generators 131 calculated by the magnetic field generator position acquisition unit 283 and image data acquired by the imaging device 110. FIG. 13 is a schematic view illustrating a display example, which indicates the position coordinates of the magnetic field generators 131 calculated by the magnetic field generator position acquisition unit 283 and the image data acquired by the imaging device 110.

According to the display example illustrated in FIG. 13, a left region 300L of a display 300 displays calculation results indicating how images of the subject coordinates projected on the imaging surface 111 are presented when viewed from the initial position of the radiation source 161. A right region 300R of the display 300 displays a captured image acquired by the imaging device 110. For example, the left region 300L displays numbers (not illustrated) assigned to respective point groups. The right region 300R is provided with a user interface (UI) configured to acquire a position of each of the spherical images from the captured image by clicking with the input device 191 around a corresponding one of the spherical images, which are associated in the order of the numbers assigned to the respective point groups. The projection coordinates may be rearranged by using the UI in the same order as the numbers assigned to the subject coordinates. Further, the detection range of an absorber 132 may be designated by clicking or dragging around a spherical image with the input device 191 upon detecting the absorber 132. In the display example illustrated in FIG. 13, the display of the left region 300L may be replaced with the display of the right region 300R, or the display of the left region 300L may be vertically aligned with the display of the right region 300R. Alternatively, only one of the left region 300L and the right region 300R may be displayed.

In the present embodiment, the processing of the absorber position calculator 284 (the first position information acquisition unit) and the processing of the radiation source position calculator 286 (the second position information acquisition unit) are performed by the same control device 180. However, the above-described processing may be performed by separate devices.

<Functional Configuration of the Control Device 180 at Time of Measuring Biomagnetic Information of Subject S>

Figure 14:
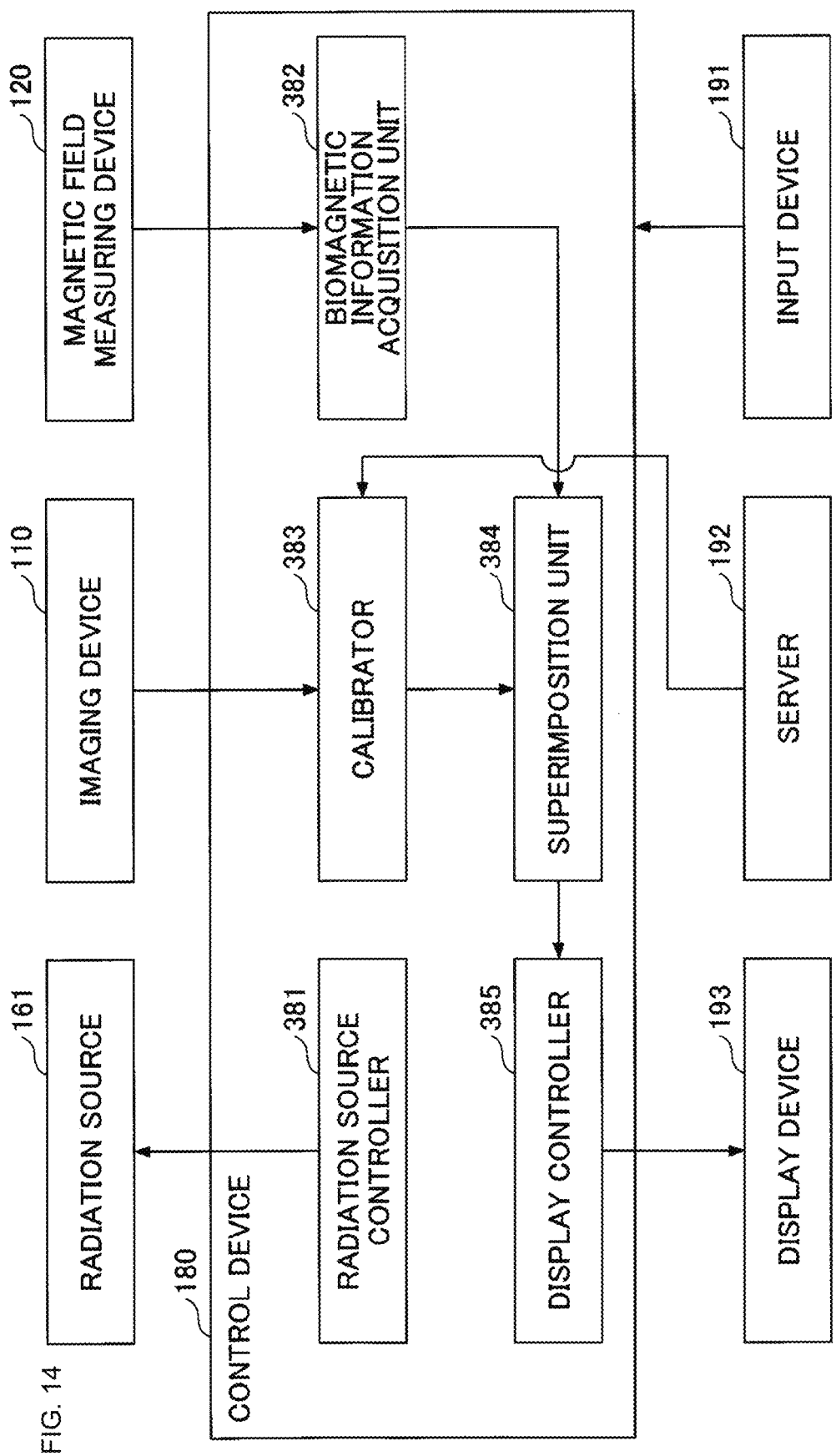
FIG. 14 is a diagram illustrating a functional configuration of a control device upon biological measurement of a subject.

At time of measuring biomagnetic information of a subject S, the control device 180 functionally includes a radiation source controller 381, a biomagnetic information acquisition unit 382, a calibrator 383, a superimposition unit 384, and a display controller 385, as illustrated in FIG. 14.

(Radiation Source Controller 381)

The radiation source controller 381 is configured to control the timing of radiation emission performed by the radiation source 161.

(Biomagnetic Information Acquisition Unit 382)

The biomagnetic information acquisition unit 382 is configured to receive signals output from the magnetic sensors 121 of the magnetic field measuring device 120, and acquire biomagnetic detection results of the subject S as biomagnetic information.

(Calibrator 383)

The calibrator 383 is configured to calibrate morphological images output from the imaging device 110 using values of the nine parameters (x0, y0, z0, xb1, yb1, zb1, θ, φ, and ψ) stored in the server 192.

(Superimposition Unit 384)

The superimposition unit 384 is configured to superimpose the biomagnetic information acquired by the biomagnetic information acquisition unit 382 on the morphological images calibrated by the calibrator 383, and deliver the superimposed images to the display controller 385.

(Display Controller 385)

The display controller 385 is configured to display the superimposed images obtained from the superimposition unit 384 on the display device 193. The display controller 385 may display not only the superimposed images obtained from the superimposition unit 384 but may also display, on the display device 193, the morphological images calibrated by the calibrator 383 or the biomagnetic information acquired by the biomagnetic information acquisition unit 382, or both the morphological images and the biomagnetic information.

In measurements of a subject S using the biomagnetic measuring system 100, the calibration tool 130 is removed from the biomagnetic measuring system 100, and a measurement area of the subject S is located on the magnetic field measuring device 120 as illustrated in FIG. 2. In this state, biomagnetic measurements using the magnetic field measuring device 120 and capturing of a radiation image such as a plain X-ray image are performed using the radiation exposure device 160 and the imaging device 110.

Either biomagnetic measurements or capturing of the radiation image may be performed first.

The biomagnetic detection results and the morphological images are input to the control device 180, where the biomagnetic detection results are obtained from the magnetic field measuring device 120, and the morphological images are digital image data of the radiation image obtained from the imaging device 110.

In the control device 180, the radiation source controller 381 causes the radiation source 161 to deliver radiation during capturing the radiation image. Then, the calibrator 383 calibrates the morphological images output from the imaging device 110 using the values of the nine parameters (x0, y0, z0, xb1, yb1, zb1, θ, φ, and ψ) stored in the server 192. The biomagnetic information acquisition unit 382 acquires biomagnetic detection results of the subject S from the magnetic field measuring device 120 as the biomagnetic information. The superimposition unit 384 superimposes the biomagnetic information acquired by the biomagnetic information acquisition unit 382 on the morphological images that have been calibrated by the calibrator 383, and delivers the superimposed images to the display controller 385. Thereafter, the display controller 385 displays the superimposed images obtained from the superimposition unit 384 on the display device 193.

In this manner, the biomagnetic measuring system 100 can perform biomagnetic measurements. In addition, during biomagnetic measurements, the biomagnetic measuring system 100 partially functions as a configuration system to calibrate a position of the radiation source 161.

The position and angle of one of or both of the radiation exposure device 160 including the radiation source 161 and the imaging surface 111 may be adjusted based on the position of the radiation source 161 calculated by the radiation source position calculator 286, the reference position of the imaging surface 111, and the slope of the imaging surface 111.

Second Embodiment

<Overview of the Biomagnetic Measuring System>

In the biomagnetic measuring system according to a second embodiment, a radiation source is disposed vertically above the subject. FIG. 15 is a perspective view illustrating a configuration of a biomagnetic measuring system according to the second embodiment. FIG. 16 is a side view illustrating a configuration of the biomagnetic measuring system according to a second embodiment. FIG. 17 is a front view illustrating a configuration of the biomagnetic measuring system according to the second embodiment. FIG. 18 is a top view illustrating a configuration of the biomagnetic measuring system according to the second embodiment. FIGS. 15 to 18 illustrate configurations upon the position of the radiation source being estimated.

As illustrated in FIGS. 15 to 18, the biomagnetic measuring system 400 according to a second embodiment includes an imaging device 410, a magnetic field measuring device 120, a calibration tool 130, a support 140, a calibration tool stabilizer 150, a radiation exposure device 460 having a radiation source 461, a table 170 (see FIG. 2), and a control device 180 (see FIG. 10, etc.). In the present specification and the drawings, a Z axis represents a vertically downward direction, an X axis represents a direction viewing from the support 140 toward the magnetic field measuring device 120, and a Y axis represents a direction orthogonal to the X axis and the Z axis in the right-handed system.

Imaging Device 410

The imaging device 410 is configured to acquire morphological images as digital image data of radiation R, which passes through a measuring area of a subject S (see FIG. 2) or the calibration tool 130. Signals detected by the imaging device 410 are sent to the control device 180. The imaging device 410 is also configured to acquire a captured image of the calibration tool 130. The imaging device 410 is an example of an imager.

The imaging device 410 may use an FPD in a manner similar to the imaging device 110. The imaging device 410 may also preferably use a film coated with a photostimulable phosphor powder. When a film coated with a photostimulable phosphor powder is used, the film is preferably fixed by an imaging plane fixture 434 so as not to bend the film. A preferable material used for the imaging plane fixture 434 may be a non-magnetic material, such as acrylic resin so as not to interfere with the measuring magnetic field.

Radiation Exposure Device 460

The radiation exposure device 460 is, for example, attached to a rail 462 for facilitating the movement of the radiation exposure device 460, and the rail 462 is secured to a ceiling or the like. The rail 462 is configured to hang a radiation source 461 so as to allow the radiation exposure device 460 to move along the X axis. The rail 462 may preferably be provided with a mechanism configured to switch between locking and unlocking of the radiation exposure device 460 with respect to the rail 462. The rail 462 may also be provided with screws or the like so as to secure the radiation exposure device 460 with respect to the rail 462. As a material used for the rail 462, a material such as a metal having strength capable of suspending the radiation exposure device 460 without deformation can be used. A mechanism, such as an arm, may be used in place of the rail 462 when the radiation exposure device 460 can be movably supported above the subject S.

The control device 180 is configured to control the imaging device 410 and the radiation exposure device 460 including the radiation source 461, instead of the imaging device 110 and the radiation exposure device 160 including the radiation source 161 in the biomagnetic measuring system 100.

Other configurations are similar to those of the first embodiment.

<Method of Estimating a Position of Radiation Source 461>

Next, a method of estimating a position of the radiation source 461 will be described. In estimating a position of the radiation source 461, a calibration tool 130 is disposed between the radiation exposure device 460 and the imaging device 410, and a magnetic field measuring device 120 is disposed beneath the calibration tool 130. The imaging device 410 is sandwiched by the imaging plane fixture 434. Then, as in the first embodiment, a position of the radiation source 461 is estimated along the flowchart illustrated in FIG. 11.

Regarding a cost function, in the second embodiment, assuming that the imaging surface 411 is oriented toward the positive z axis at an initial state, and a normal vector to the imaging surface 411 is (0, 0, −1), the imaging surface 411 is represented by Math. 7 using a reference point of the projection coordinates and the normal vector.

$$-\cos(\varphi)\cos(\psi)(z - zb1) +$$
$$(\sin(\varphi)\cos(\theta) - \cos(\varphi)\sin(\psi)\sin(\theta))(y - yb1) +$$
$$(-\sin(\varphi)\sin(\theta) - \cos(\varphi)\sin(\psi)\cos(\theta))(x - xb1) = 0$$

[Math. 7]

Then, assuming that the i-th subject coordinates are (xai, yai, zai), a straight line connecting the radiation source 461 and the i-th subject coordinates is represented by Math. 5, as in the first embodiment. Accordingly, a position of the radiation source 461 can be estimated in the same manner as in the first embodiment.

The biomagnetic measuring system 400 can perform biomagnetic measurements, in a manner similar to the biomagnetic measuring system 100, using the radiation exposure device 460 including the imaging device 410 and the radiation source 461, in place of the radiation exposure device 160 including the imaging device 110 and the radiation source 161. Also, at the time of biomagnetic measurements, the biomagnetic measuring system 400 can partially function as a calibration system to calibrate a position of the radiation source 461.

The position and angle of the radiation exposure device 460 including the radiation source 461 or the imaging surface 411, or of both the radiation exposure device 460 and the imaging surface 411 may be adjusted based on the position of the radiation source 461 calculated by the radiation source position calculator 286, the reference position of the imaging surface 411, and the slope of the imaging surface 411.

(Modification of Second Embodiment)

Next, a modification of the second embodiment will be described. The modification of the second embodiment differs from the second embodiment primarily in the arrangement of the magnetic field measuring device 120, the imaging device 410, and the radiation exposure device 460. FIG. 19 is a front view illustrating a configuration of a biomagnetic measuring system according to the modification of the second embodiment.

In the modification of the second embodiment, an upper surface of the magnetic field measuring device 120 is tilted from a horizontal plane (X-Y plane) as illustrated in FIG. 19. As a result, the imaging surface 411 of the imaging device 410 is also tilted from the horizontal plane. The radiation source 461 included in the radiation exposure device 460 is then located on the normal to the imaging surface 411. For example, a line connecting the center of the imaging surface 411 and the center of the radiation source 461 intersects the imaging surface 411 at right angles. The magnitude of the tilt is, for example, 10 degrees.

In the modification of the second embodiment, it is possible to provide the same effects as in the second embodiment.

Note that in the first embodiment, the upper surface of the magnetic field measuring device 120 may be tilted from the horizontal plane, the imaging surface 111 of the imaging device 110 may be tilted from the horizontal plane (the X-Y plane), and the radiation source 161 included in the radiation exposure device 160 may be located on the normal to the imaging surface 111, in a manner similar to the modification of the second embodiment.

Although the preferred embodiments have been described in detail above, various modifications and substitutions may be made to the above-described embodiments without departing from the scope of the claims.

REFERENCE SIGNS LIST 100, 400 biomagnetic measuring system
110, 410 imaging device
111, 411 imaging surface
120 magnetic field measuring device
121 magnetic sensor
130 calibration device
131 magnetic field generator
132 absorber
133 support
160, 460 radiation exposure device
161, 461 radiation source
180 control device
191 input device
192 server
193 display device
281 radiation source controller
282 relative position acquisition unit
283 magnetic field generator position acquisition unit
284 absorber position calculator
285 absorber image detector
286 radiation source position calculator
287 display controller
381 radiation source controller
382 biomagnetic information acquisition unit
383 calibrator
384 superimposition unit
385 display controller The present application is based on Japanese Priority Application No. 2019-120422 filed on Jun. 27, 2019, and Japanese Priority Application No. 2019-166562 filed on Sep. 12, 2019, the entire contents of which are hereby incorporated herein by reference.

The invention claimed is:

1. A radiation source position estimation system comprising:
    a processor; and
    a memory storing program instructions;
    a first position information specifier stored in the memory to cause the processor to execute the program instructions configured to specify position information of one or more elements included in a position measuring member;
    an imager configured to acquire images of the one or more elements formed by radiation emitted from a radiation source;
    a second position information specifier stored in the memory to cause the processor to execute the program instructions configured to specify position information of the radiation source, based on the position information specified by the first position information specifier and the images acquired by the imager; and
    a detector configured to detect position information of one or more magnetic field generators, based on magnetic fields generated by the one or more magnetic field generators, wherein
    the position measuring member includes the one or more magnetic field generators, and the radiation source includes one or more of an X-ray source, an α-ray source, a β-ray source, or a γ-ray source.

2. The radiation source position estimation system according to claim 1, wherein
    each of the one or more elements is an absorber configured to absorb the radiation emitted by the radiation source, the position measuring member includes a support configured to support the one or more elements, and the support lets through radiation more than the absorber lets through.

3. The radiation source position estimation system according to claim 1, wherein the imager has an imaging surface disposed such that the one or more elements are interposed between the imaging surface and the radiation source.

4. The radiation source position estimation system according to claim 3, wherein the imager includes an image detector configured to detect the images formed on the imaging surface.

5. The radiation source position estimation system according to claim 4, wherein the one or more elements each have a spherical shape, and the image detector includes a circle detector configured to detect a circle.

6. The radiation source position estimation system according to claim 1, further comprising:

a display controller configured to selectively display, on a display device, the position information specified by the first position information specifier or the images, or both the position information specified by the first position information specifier and the images acquired by the imager.

7. The radiation source position estimation system according to claim 6, wherein the display controller selectively displays the images on the display device.

8. A calibration system comprising:

the radiation source position estimation system according to claim 1; and a calibrator configured to calibrate morphological images based on a position of the radiation source specified by the second position information specifier, the morphological images being acquired by radiation imaging performed by using the radiation source and the imager.

9. A biomagnetic measuring system comprising:

the calibration system according to claim 8; and a radiation source configured to form the images, wherein the position measuring member includes one or more magnetic field generators, the radiation source position estimation system includes a magnetic field measuring device configured to detect position information of the one or more magnetic field generators, based on magnetic fields generated by the one or more magnetic field generators, a radiation image of a subject is acquired by the radiation source and the imager, and biomagnetic detection of the subject is performed by the magnetic field measuring device.

10. The biomagnetic measuring system according to claim 9, wherein the radiation source is disposed along a horizontal direction with respect to the subject.

11. The biomagnetic measuring system according to claim 9, wherein the radiation source is disposed vertically above the subject.

12. The biomagnetic measuring system according to claim 9, comprising:

a superimposition unit configured to superimpose biomagnetic detection results of the subject acquired by the magnetic field measuring device on morphological images calibrated by the calibrator.

* * * * *